US007186815B2

(12) United States Patent
Ravn et al.

(10) Patent No.: US 7,186,815 B2
(45) Date of Patent: Mar. 6, 2007

(54) **METHOD OF ISOLATING SECRETION SIGNALS IN LACTIC ACID BACTERIA AND NOVEL SECRETION SIGNALS ISOLATED FROM *LACTOCOCCUS LACTIS***

(75) Inventors: Peter Ravn, Naerum (DK); Soeren Michael Madsen, Copenhagen N (DK); Astrid Vrang, Lyngby (DK); Hans Israelsen, Alleroed (DK); Mads Groenvold Johnsen, Frederiksberg C (DK); Lars Bredmose, Copenhagen N (DK); José Arnau, Hellerup (DK)

(73) Assignee: Bioneer A/S, Hørsholm (DK)

( * ) Notice: Subject to any disclaimer, the term of this patent is extended or adjusted under 35 U.S.C. 154(b) by 131 days.

(21) Appl. No.: 10/431,577

(22) Filed: May 8, 2003

(65) Prior Publication Data

US 2004/0038263 A1 Feb. 26, 2004

Related U.S. Application Data

(63) Continuation of application No. 09/601,764, filed as application No. PCT/DK00/00437 on Aug. 4, 2000, now abandoned.

(30) Foreign Application Priority Data

Aug. 6, 1999 (DK) ............................. 1999 01105

(51) Int. Cl.
*C07H 21/02* (2006.01)
*C07H 21/04* (2006.01)
*C07N 7/00* (2006.01)
*C07N 15/00* (2006.01)
*C07N 15/09* (2006.01)

(52) U.S. Cl. .................. 536/23.1; 536/24.1; 435/320.1
(58) Field of Classification Search .................. 435/6, 435/320.1; 536/23.1, 24.1
See application file for complete search history.

(56) References Cited

U.S. PATENT DOCUMENTS 4,914,025 A 4/1990 Manoil et al.
5,529,908 A 6/1996 Palva et al.

FOREIGN PATENT DOCUMENTS

| WO | WO 92/04451 | 3/1992 |
| WO | WO 94/16086 | 7/1994 |
| WO | WO 96/41891 | 12/1996 |
| WO | WO 98/10079 | 3/1998 |
| WO | WO 00/06736 | 2/2000 |

OTHER PUBLICATIONS

Poquet et al An export specific reporter designed for gram-positive bacteria: Application to *Lactococcus lactis* 1998 Journal of Bacteriology 180:1904-1912.*
Madsen et al. Molecular Microbiology 1999 vol. 32 pp. 75-87.*
Ravn et al., Optimizaton of signal peptide SP310 for heterologous protein production in *Lactococcus lactis*, Microbiology (2003), vol. 149, pp. 2193-2201.
European Search Report dated Jul. 6, 2004 for European Application No. 00951271.6.
European Standard Search Report for DK PA 1999 01105.
Isabelle Poquet et al., An Export-Specifi Reporter Designed for Gram-Positive Bacteria: Application to *Lactococcus lactis*, Journal of Bacteriology, Apr. 1998, p. 1904-1912, vol. 180, No. 7 (XP-002135834).
Hans Isrealsen et al., Cloning and Partial Characterization of Regulated Promoters from *Lactococcus lactis* Tn917-lacZ Integrants with the New Promoter Probe Vector, pAK80, Applied and Environmental Microbiology, Jul. 1995, p. 2540-2547, vol. 61, No. 7 (XP-002135836).
M. Tadayyon and Jenny K. Broome-Smith, Tn*blaM:* a transposon for directly tagging bacterial genes encoding cell envelope and secreted proteins, Gene, 111 (1992) 21-26 (XP-000605471).
Hans Isrealsen and Egon Bech Hansen, Insertion of Transposon Tn*917* Derivatives into the *Lactococcus lactis* subsp. *lactis* Chromosome, Applied and Enviromental Microbiology, Jan. 1993, p. 21-26, vol. 59, No. 1 (XP-000891981).
Y. Le Loir et al., Direct Screening of Recombinants in Gram-Positive Bacteria Using the Secreted Staphylococcal Nuclease as a Reporter, Journal of Bacteriology, Aug. 1994, p. 5135-5139, vol. 176, No. 16 (XP-000857662).
P. Langella and Y. Le Loir, Heterologous protein secretion in *Lactococcus lactis:* a novel antigen delivery system, Brazilian Journal of Medical and Biological Research (1999) 32:191-198 (XP-000857556).
Mervi Sibakov et al., Secretion of TEM 3-Lactamase with Signal Sequences Isolated from the Chromosome of *Lactococcus lactis* subsp. *lastic,* Applied and Environmental Microbiology, Feb. 1991, p. 341-348, vol. 57, No. 2 (XP-00891892).
Gaspar Perez-Martinez et al., Protein export elements from Lactococcus lastis, Mol Gen Genet (1992) 234:401-411 (XP-002135837).
Hilde Smith et al., Construction and Use of Signal Sequence Slection Vectors in *Escherichia coli* and *Bacillus subtilis*, Journal of Bacteriology, Jul. 1987, p. 3321-3328, vol. 169, No. 7 (XP-000610632).
Hilde Smith et al., Characterization of signal-sequence-coding regions selected from the *Bacillus subtilis* chromosome, Gene 70 (1988) 351-361 (XP-000000377).

(Continued)

*Primary Examiner*—James Ketter
*Assistant Examiner*—Konstantina Katcheves
(74) *Attorney, Agent, or Firm*—Hunton & Williams LLP

(57) ABSTRACT

A method of identifying nucleotide sequences coding for signal peptides in lactic acid bacteria, using a DNA molecule comprising a transposon including a promoterless reporter gene from which DNA molecule a region between the LR and the reporter gene is deleted and the DNA molecule comprises a DNA sequence coding for a secretion reporter molecule. By deleting the region between the LR and the reporter gene, stop codons in-frame with the secretion reporter molecule is removed which upon transposition permits translational fusions from upstream the LR.

13 Claims, 5 Drawing Sheets

OTHER PUBLICATIONS

Figure 1A:
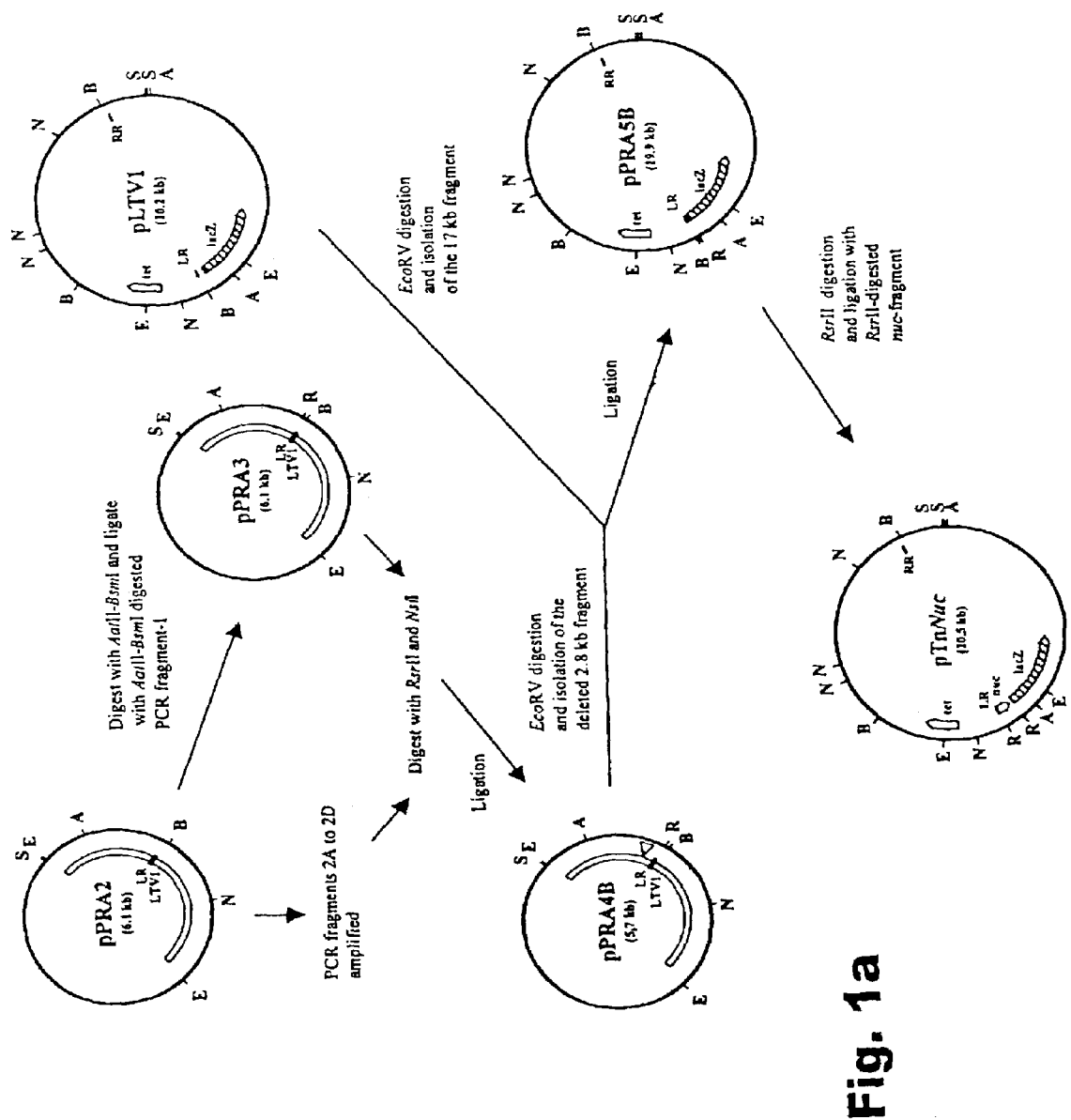

Peter Ravn et al., The development of TnNuc and its for the isolation of novel secretion signals in *Lactococcus lactis*, Gene 242 (2000) 347-356 (XP-002135839).

Cameron D. Ashbaugh et al., Molecular Analysis of the Capsule Gene Region of Group A *Streptococcus:* the *has*AB Genes Are Sufficient for Capsule Expression, Journal of Bacteriology, Sep. 1998, p. 4955-4959, vol. 180, No. 18.

Andrew Camilli et al., Insertional mutagenesis of *Listeria monocytogenes* with a Novel Tn*917* Derivative That Allows Direct Cloning of DNA Flanking Transposon Insertions, Journal of Bacteriology, Jul. 1990, p. 3738-3744, vol. 172, No. 7.

Mario Chen et al., Effect of Alteration of Charged Residues at the N Termini of Signal Peptides on Protein Export in *Bacillus subtilis,* Journal of Bacteriology, Sep. 1994, p. 5796-5801, vol. 176, No. 18.

Huanfeng Chen et al., Competition between Functional Signal Peptides Demonstrates Variation in Affinity for the Secretion Pathway, Journal of Bacteriology, Dec. 1996, p. 6658-6664, vol. 178, No. 23.

David N. Collier- *Escherichia coli* Signal Peptides Direct inefficient Secretion of an Outer Membrane Protein (OmpA) and Periplasmic Proteins (Maltose-Binding Protein, Ribose-Binding Protein, and Alkaline Phosphatase) in *Bacillus subtilis* , Journal of Bacterilogy, May 1994, p. 3013-3020, vol. 176, No. 10.

Michael J. Gasson, Plasmid Complements of *Streptococcus lactis* NCDO 712 and Other Lactic Streptococci After Protoplast-Induced Curing, Journal of Bacterilology, Apr. 1983, p. 1-9, vol. 154, No. 1.

Jean-Jacques Godon et al., The *Lactococcus lactis* sex-factor aggregation gene *cluA* , Molecualr Microbiology (1994), 12(4), 655-663.

Seth G.N. Grant et al.,, Differential Plasmid rescue from transgenic mouse DNAs into *Escherichia coli* methylation-restriction mutants, Proc. Natl., Acad. Sci. USA, vol. 87, pp. 4645-4649, Jun. 1990.

Helge Holo et al., High-Frequency Transformaton, by Electroporation, of *Lactococcus lactis* subsp. *cremoris* Grown with Glycine in Osmotically Stabilized Media, Applied and Environmental Microbiology, Dec. 1989, p. 3119-3123, vol. 55, No. 12.

Peter Ruhdal Jensen et al., Minimal Requirements for Exponential Growht of *Lactococcus Lactis*, Applied and Environmental Microbiology, Dec. 1993, p. 4363-4366, vol. 59, No. 12.

Jennifer W. Izard, et al., Physical and Conformational Properties of Synthetic Idealized Signal Sequences Parallel Their Biological Function, Biochemistry, 1995, 34, 9904-9912.

Jennifer W. Izard et al., The Amino-terminal Charge and Core Region Hydrophobicity Interdependently Contribute to the Function of Signal Sequences, The Journal of Biological Chemistry, vol. 271, No. 35, Issue of Aug. 30, p. 51579-21582.

R.V.F. Lachica et al., Metachromatic Agar-Diffusion Methods for Detecting Staphylococcal Nuclease Activity, Appl. Microbiol., p. 585-587, vol. 21, 1971.

Colin Manoil and Jon Beckwith, Tn*pho*A: A transposon probe for protein export signals, Proc. Natl. Acad. Sct. USA, vol. 82, pp. 8129-8133, Dec. 1985 (XP-002135835).

Søren M. Madsen et al., Cloning and Transcriptional Analysis of Two Threonine Biosynthetic Genes from *Lactococcus lactis* MG1614, Journal of Bacterilogy, Jul. 1996, p. 3689-3694, vol, 178, No. 13.

Søren M. Madsen et al., Molecualr characterization of the pH-inducible and growth phase-dependent promoter P170 of *Lactococcus lactis*, Molecular Microbiology (1999) 32(1), 75-87.

Bruno Martoglio et al., Signal Sequences: more than just greasy peptides, Trends in Cell Biology (vol. 8), Oct. 1998, p. 410-415.

Henrik Neilsen et al., A Neural Network Method for Identification of Prokaryotic and Eukaryotic Signal Peptides and Prediction of Their Cleavage Sites, International Journal of Neural Systems, vol. 8, Nos. 5&6, (Oct./Dec. 1997), 581-599.

Claire-Lise Santini et al., A novel Sec-independent periplasmic protein translocation pathway in *Escherichia coli*, The EMBO Journal, vol. 17, No. 1, pp. 101-112, 1998.

A. Mark Settles et al., Old and New pathways of Protein Export in Chloroplasts and Bacteria, Trends in Cells Biology (vol. 8) Dec. 1998, p. 494-501.

David Sherratt, "Tn3 and Related Transposable Elements: Site-Specific Recombination and Transposition", In: Berg, E.D. and Howe, M.M. (eds.) Mobile DNA, American Society for Microbiology, Washington, D.C., p. 163-184.

Craig Stephens, Protein Secretion: Getting folded proteins across membranes, Current Biology 1998, 8:R578-R581.

Yasushi Takimura et al., Secretion of Human Interlukin-2 in Biologically Active Form by *Bacillus brevis* Directly into Culture Medium, Biosci. Biotech. Biochem. 61 (11), 1858-1861, 1997.

Martien van Asseldonk et al., Cloning of *usp*45, a gene encoding a secreted protein from *Lactococcus lactis* subsp. *lactis* MG1363, Gene, 95 (1990) 155-160.

Martien van Asseldonk et al., Funtional analysis of the *Lactocuccus lactis usp45* secretion signal in the secretionof a homologous proteinase and a heterologous α-amylase, Mol. Gen. Genet (1993) 240:428-434.

Gunnar von Heijne et al., The Signal Peptide, J. Membrane Biol. 115, 195-201 (1990).

Lin-Fa Wang et al., Use of a Gram signal peptide for protein secretion by Gram hosts: basic protease of *Dichelobacter nodosus* is produced and secreted by *Bacillus subtilis*, Gene, 131(1993) 97-102.

Joel J. Weiner et al., A Novel and Ubiquitous System for Membrane Targeting and Secretion of Cofactor-Containing Proteins, Cell, vol. 93, 93-101, Apr. 3, 1998.

G.C. Whiting et al., Metabolism of polysaccharides by the *Streptococcus mutans dexB* gene product, Journal of General Microbiology (1993), 139, 2019-2026.

Manfred Lansing et al., Hyaluronate synthase: cloning and sequencing of the gene from *Streptococcus* sp., Biochem. J. (1993), 289, 179-184.

Philip Youngman, Plasmid vectors for recovering and exploiting Tn917 tranpositions in Bacilus and other Gram-Positive bacteria, *In* Hardy, K.G. (ed), Plasmids A Practical Approach, Chapter 4, IRL Press, pp. 79-103.

Debra M. Sauvé, Concentration of Dilute Protein for Gel Electrophoresis, Analytical Biochemistry 226, 382-383 (1995).

European Standard Search Report for DK PA 1999 01105.

* cited by examiner

| Plasmid | Deleted Region | Sequence Position | Transposition |
|---|---|---|---|
| pPRA5A | ——— | 13647-13374 | − |
| pPRA5B | ——— | 13626-13374 | + |
| pPRA5C | ——— | 13608-13374 | + |
| pPRA5D | —— | 13589-13374 | + |

SEQUENCE LISTING

<160> NUMBER OF SEQ ID NOS: 66

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 1
cgatgaatgc cggaccgaat tgatacacta atgcttttat ataggg        46

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
gtgtagtcgg tttatgcagc        20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
cacacatacc aatacatgc        19

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
gcatcggtcc gtaggcgctc gggacccc        28

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 5
gcatcggtcc gttcttatcg atacaaattc ctcg        34

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 6
gcatcggtcc gaaattttta aatctatttc ttatc        35

<210> SEQ ID NO 7
<211> LENGTH: 36

```
<212> TYPE: DNA
<213> ORGANISM: Artificial Sequence
<220> FEATURE:
<223> OTHER INFORMATION: Description of Artificial Sequence: Primer

<400> SEQUENCE: 7
gcatcggtcc gtaaatgtac aaaataacag cgaaat                              36

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
gcatcggacc gtcacaaaca gataacggcg                                     30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gcatcggtcc gcattattga cctgaatcag                                     30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
ggaagatctt cacaaacaga taacggc                                        27

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 11
acgcgtcgac gaattcgatc taaaattata aaagtgcc                            38

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 12
gcatcccggg tctagattag ggtaactttg aaaggatatt cctcatgaaa aaaacattga    60
gagaccagtt acttg                                                     75

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Primer
```

```
<400> SEQUENCE: 13
gcatagatct actccaacta tcacctgttg catttgctc                           39

<210> SEQ ID NO 14
<211> LENGTH: 76
<212> TYPE: DNA
<213> ORGANISM: Artificial Sequence
<220> FEATURE:
<223> OTHER INFORMATION: Description of Artificial Sequence: Primer

<400> SEQUENCE: 14
gcatcccggg tctagattag ggtaactttg aaaggatatt cctcatgaat aaatcaaaaa    60
ttattgcttt ctctgc                                                   76

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 15
gcatagatct atcaatggaa ttaacatcag ctgccatgc                           39

<210> SEQ ID NO 16
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 16
gcatcccggg tctagattag ggtaactttg aaaggatatt cctcatgaaa tttataaaaa    60
aaagagttgc aatagcc                                                  77

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 17
gcatagatct gttatcatta aaatcactcc gattaagag                           39

<210> SEQ ID NO 18
<211> LENGTH: 72
<212> TYPE: DNA
<213> ORGANISM: Artificial Sequence
<220> FEATURE:
<223> OTHER INFORMATION: Description of Artificial Sequence: Primer

<400> SEQUENCE: 18
tagtaggatc ccgggtctag attagggtaa ctttgaaagg atattcctca tgaaaaaaaa    60
gattatctca gc                                                       72

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 19
```
acgcgtcgac ctgcagagat cttgtgtcag cgtaaacacc                            40

<210> SEQ ID NO 20
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 20
gcatcccggg tctagattag ggtaactttg aaaggatatt cctcatgaaa tttaataaaa    60
aaagagttgc aatagcc                                                     77

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 21
ctattggttt gattacgtcg gctttctaga tacg                                  34

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 22
ggttctattg gttcgattac gtcggctttc tagatacg                              38

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 23
gttatagtag ttaggttcta cgagttcgtc ggctttctag atacg                      45

<210> SEQ ID NO 24
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 24
ctataaacat tcaaaaaaat gttattaggg tttgtgacga gttcgtcggc tttctagata     60
cg                                                                     62

<210> SEQ ID NO 25
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 25
ctataaacat tcaaaaaaat gttattaggt tttggtttga ttacgtcggc tttctagata     60

```
cg                                                               62

<210> SEQ ID NO 26
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 26
ctataaacat tcaaaaaaat gttattaggt tttggttcga ttacgtcggc tttctagata     60
cg                                                               62

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 27
gttatagtag ttaggttcta cgagttcgtc tatgatctag atacg                    45

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 28
gttatagtag ttagctacga gttcgtcggc tttctagata cg                       42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 29
gttatagtag ttaggttcga gttcgtcggc tttctagata cg                       42

<210> SEQ ID NO 30
<211> LENGTH: 88
<212> TYPE: DNA
<213> ORGANISM: Artificial Sequence
<220> FEATURE:
<223> OTHER INFORMATION: Description of Artificial Sequence: Primer

<400> SEQUENCE: 30
cgttatcggt gcaaataaaa aaactataaa cattcaaaaa aatgttatag tagttaggtt     60
ctacgagttc gtcggctttc tagatacg                                       88

<210> SEQ ID NO 31
<211> LENGTH: 88
<212> TYPE: DNA
<213> ORGANISM: Artificial Sequence
<220> FEATURE:
<223> OTHER INFORMATION: Description of Artificial Sequence: Primer

<400> SEQUENCE: 31
cgttatcggt gcaaataaaa aaactataaa cataaaaaaa aatgttatag tagttaggtt     60
ctacgagttc gtcggctttc tagatacg                                       88
```

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Primer

<400> SEQUENCE: 32
cctcccgggt ctagattagg gtaactttga aaggatattc ctcatgaaat ttaataaaaa       60
aagagttgca atagccttgt ttattgcttt gatatttgta cttttttttc ttatatcatc      120

<210> SEQ ID NO 33
<211> LENGTH: 120
<212> TYPE: DNA
<213> ORGANISM: Artificial Sequence
<220> FEATURE:
<223> OTHER INFORMATION: Description of Artificial Sequence: Primer

<400> SEQUENCE: 33
cctcccgggt ctagattagg gtaactttga aaggatattc ctcatgaaat ttaataaaaa       60
aagagttctt atactttgt ttattctttt gatatttgta cttttttttc ttatatcatc      120

<210> SEQ ID NO 34
<211> LENGTH: 103
<212> TYPE: DNA
<213> ORGANISM: Artificial Sequence
<220> FEATURE:
<223> OTHER INFORMATION: Description of Artificial Sequence: Primer

<400> SEQUENCE: 34
cctcccgggt ctagattagg gtaactttga aaggatattc ctcatgaaat ttaataaaaa       60
aagacttttg cttttgcttt tgcttttgct tttacttctt ttg                       103

<210> SEQ ID NO 35
<211> LENGTH: 73
<212> TYPE: DNA
<213> ORGANISM: Artificial Sequence
<220> FEATURE:
<223> OTHER INFORMATION: Description of Artificial Sequence: Primer

<400> SEQUENCE: 35
gaaaatgaag aaaacgaaaa cgaatatagt agttaggttc tattggtttg attacgtcgg       60
ctttctagat acg                                                         73

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 36
ggttctattg gttcgattac gtcggctttc tagatacg                              38

<210> SEQ ID NO 37
<211> LENGTH: 120
<212> TYPE: DNA
<213> ORGANISM: Artificial Sequence
<220> FEATURE:
<223> OTHER INFORMATION: Description of Artificial Sequence: Primer

<400> SEQUENCE: 37

-continued

```
cctcccgggt ctagattagg gtaactttga aaggatattc ctcatgaaat ttaataaaaa      60
aagagttctt atactttgt ttattctttt gatatttgta cttttttttc ttatatcatc     120
```

<210> SEQ ID NO 38
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 38

```
gcatcccggg tctagattag ggtaactttg aaggatatt cctcatgaaa ataaaaaaa       60 gagttgcaat agcc                                                       74
```

<210> SEQ ID NO 39
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 39

```
gcatcccggg tctagattag ggtaactttg aaggatatt cctcatgaaa tttaaaaaaa      60
gagttgcaat agcc                                                       74
```

<210> SEQ ID NO 40
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 40

```
gcatcccggg tctagattag ggtaactttg aaggatatt cctcatgaaa tttaaaaaaa      60
aaagagttgc aatagcc                                                    77
```

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 41

Met Lys Phe Asn Lys Lys Arg Val Ala Ile Ala Thr Phe Ile Ala Leu
1               5                   10                  15

Ile Phe Val Ser Phe Phe Thr Ile Ser Ser Ile Gln Asp Asn Gln Thr
            20                  25                  30

Asn Ala Ala Glu Arg Ser
        35

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 42

Met Lys Phe Asn Lys Lys Arg Val Ala Ile Ala Thr Phe Ile Ala Leu
1               5                   10                  15

```
Ile Phe Val Ser Phe Phe Thr Ile Ser Ser Ile Gln Asp Asn Gln Ala
            20                  25                  30

Asn Ala Ala Glu Arg Ser
            35

<210> SEQ ID NO 43
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 43

Met Lys Phe Asn Lys Lys Arg Val Ala Ile Ala Thr Phe Ile Ala Leu
 1               5                  10                  15

Ile Phe Val Ser Phe Phe Thr Ile Ser Ser Ile Gln Asp Ala Gln Ala
            20                  25                  30

Ala Glu Arg Ser
            35

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 44

Met Lys Phe Asn Lys Lys Arg Val Ala Ile Ala Thr Phe Ile Ala Leu
 1               5                  10                  15

Ile Phe Val Ser Phe Phe Thr Ile Ile Pro Asn Thr Ala Gln Ala Ala
            20                  25                  30

Glu Arg Ser
            35

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 45

Met Lys Phe Asn Lys Lys Arg Val Ala Ile Ala Thr Phe Ile Ala Leu
 1               5                  10                  15

Ile Phe Val Ser Phe Phe Thr Ile Ile Gln Asn Gln Thr Asn Ala Ala
            20                  25                  30

Glu Arg Ser
            35

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 46

Met Lys Phe Asn Lys Lys Arg Val Ala Ile Ala Thr Phe Ile Ala Leu
```

-continued

```
                1               5                  10                 15
Ile Phe Val Ser Phe Phe Thr Ile Ile Gln Asn Gln Ala Asn Ala Ala
                        20                  25                 30

Glu Arg Ser
        35
```

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 47

```
Met Lys Phe Asn Lys Lys Arg Val Ala Ile Ala Thr Phe Ile Ala Leu
1               5                   10                  15

Ile Phe Val Ser Phe Phe Thr Ile Ser Ser Ile Gln Asp Ala Gln Ala
                        20                  25                  30

Asp Thr Arg Ser
        35
```

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 48

```
Met Lys Phe Asn Lys Lys Arg Val Ala Ile Ala Thr Phe Ile Ala Leu
1               5                   10                  15

Ile Phe Val Ser Phe Phe Thr Ile Ser Ser Ile Asp Ala Gln Ala Ala
                        20                  25                  30

Glu Arg Ser
        35
```

<210> SEQ ID NO 49
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 49

```
Met Lys Phe Asn Lys Lys Arg Val Ala Ile Ala Thr Phe Ile Ala Leu
1               5                   10                  15

Ile Phe Val Ser Phe Phe Thr Ile Ser Ser Ile Gln Ala Gln Ala Ala
                        20                  25                  30

Glu Arg Ser
        35
```

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 50

```
Met Lys Phe Asn Lys Lys Arg Val Ala Ile Ala Thr Phe Ile Ala Leu
 1               5                  10                  15

Ile Phe Val Ser Phe Phe Thr Ile Ser Ser Ile Gln Asp Ala Gln Ala
                20                  25                  30

Ala Glu Gly Ser
            35
```

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 51

```
Met Lys Phe Asn Lys Lys Arg Val Ala Ile Ala Thr Phe Ile Phe Leu
 1               5                  10                  15

Ile Phe Val Ser Phe Phe Thr Ile Ser Ser Ile Gln Asp Ala Gln Ala
                20                  25                  30

Ala Glu Arg Ser
            35
```

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 52

```
Met Lys Phe Asn Lys Lys Arg Val Ala Ile Ala Thr Phe Ile Phe Leu
 1               5                  10                  15

Ile Phe Val Phe Phe Phe Thr Ile Ser Ser Ile Gln Asp Ala Gln Ala
                20                  25                  30

Ala Glu Arg Ser
            35
```

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 53

```
Met Lys Phe Asn Lys Lys Arg Val Ala Ile Ala Leu Phe Ile Ala Leu
 1               5                  10                  15

Ile Phe Val Leu Phe Phe Leu Ile Ser Ser Ile Gln Asp Asn Gln Thr
                20                  25                  30

Asn Ala Ala Glu Arg Ser
                    35
```

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 54

Met Lys Phe Asn Lys Lys Arg Val Leu Ile Leu Leu Phe Ile Leu Leu
1               5                   10                  15

Ile Phe Val Leu Phe Phe Leu Ile Ser Ser Ile Gln Asp Asn Gln Thr
                20                  25                  30

Asn Ala Ala Glu Arg Ser
        35

<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 55

Met Lys Phe Asn Lys Lys Arg Leu Leu Leu Leu Leu Leu Leu Leu Leu
1               5                   10                  15

Leu Leu Leu Leu Leu Leu Leu Ile Ser Ser Ile Gln Asp Asn Gln Thr
                20                  25                  30

Asn Ala Ala Glu Arg Ser
        35

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 56

Met Lys Phe Asn Lys Lys Arg Val Ala Ile Ala Leu Phe Ile Ala Leu
1               5                   10                  15

Ile Phe Val Leu Phe Phe Leu Ile Ser Ser Ile Gln Asp Asn Gln Ala
                20                  25                  30

Asn Ala Ala Glu Arg Ser
        35

<210> SEQ ID NO 57
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 57

Met Lys Phe Asn Lys Lys Arg Val Leu Ile Leu Leu Phe Ile Leu Leu
1               5                   10                  15

Ile Phe Val Leu Phe Phe Leu Ile Ser Ser Ile Gln Asp Asn Gln Ala
                20                  25                  30

Asn Ala Ala Glu Arg Ser
        35

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

```
<400> SEQUENCE: 58

Met Lys Asn Lys Lys Arg Val Ala Ile Ala Thr Phe Ile Ala Leu Ile
 1               5                  10                  15

Phe Val Ser Phe Phe Thr Ile Ser Ser Ile Gln Asp Ala Gln Ala Ala
             20                  25                  30

Glu Arg Ser
        35

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 59

Met Lys Asn Lys Lys Arg Val Ala Ile Ala Thr Phe Ile Ala Leu Ile
 1               5                  10                  15

Phe Val Ser Phe Phe Thr Ile Ser Ser Ile Asp Ala Gln Ala Ala Glu
             20                  25                  30

Arg Ser

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 60

Met Lys Phe Lys Lys Arg Val Ala Ile Ala Thr Phe Ile Ala Leu Ile
 1               5                  10                  15

Phe Val Ser Phe Phe Thr Ile Ser Ser Ile Gln Asp Ala Gln Ala Ala
             20                  25                  30

Glu Arg Ser
        35

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 61

Met Lys Asn Lys Lys Arg Val Ala Ile Ala Thr Phe Ile Phe Leu Ile
 1               5                  10                  15

Phe Val Phe Phe Phe Thr Ile Ser Ser Ile Gln Asp Ala Gln Ala Ala
             20                  25                  30

Glu Arg Ser
        35

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence: Synthetic
      amino acid sequence
```

-continued

```
<400> SEQUENCE: 62

Met Lys Phe Lys Lys Arg Val Ala Ile Ala Thr Phe Ile Ala Leu
 1               5                  10                  15

Ile Phe Val Ser Phe Phe Thr Ile Ser Ser Ile Gln Asp Ala Gln Ala
                20                  25                  30

Ala Glu Arg Ser
            35

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 63

Met Lys Lys Lys Ile Ile Ser Ala Ile Leu Met Ser Thr Val Ile Leu
 1               5                  10                  15

Ser Ala Ala Ala Pro Leu Ser Gly Val Tyr Ala Asp Thr Asn Ser Asp
                20                  25                  30

<210> SEQ ID NO 64
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 64

Met Gln Arg Lys Lys Lys Gly Leu Ser Ile Leu Leu Ala Gly Thr Val
 1               5                  10                  15

Ala Leu Gly Ala Leu Ala Val Leu Pro Val Gly Glu Ile Gln Ala Lys
                20                  25                  30

Ala Ala Ile Ser Gln Gln
            35

<210> SEQ ID NO 65
<211> LENGTH: 45
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 65

Met Lys Asn Leu Ile Pro Lys Lys Ile Lys Gln Val Gly Ile Leu Val
 1               5                  10                  15

Gly Ala Leu Leu Met Leu Leu Ser Val Leu Pro Val Asn Leu Leu Gly
                20                  25                  30

Val Met Lys Val Asp Ala Asp Ser Ser Gln Thr Glu Val
            35                  40                  45

<210> SEQ ID NO 66
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 66
```

```
Met Lys Lys Ile Ala Ile Ile Phe Cys Thr Leu Leu Met Ser Leu Ser
 1           5               10                  15

Val Leu Ser Ser Phe Ala Val Ser Ala Asp Thr Thr Thr Thr Thr Asn
            20              25                  30

Asn
```

METHOD OF ISOLATING SECRETION SIGNALS IN LACTIC ACID BACTERIA AND NOVEL SECRETION SIGNALS ISOLATED FROM *LACTOCOCCUS LACTIS*

CROSS-REFERENCE TO RELATED APPLICATIONS

This application is a continuation of U.S. application Ser. No. 09/601,764, filed Aug. 8, 2000, which is a national phase application of International Application No. PCT/DK00/00437, filed Aug. 4, 2000, which claims priority to Denmark Application No. 1999 01105, filed Aug. 6, 1999.

FIELD OF INVENTION

The present invention relates to the field of microbial expression systems, in particular to means of improving the level of secretion of homologous or heterologous gene products in recombinant host cells. Specifically, there is provided the means of identifying and isolating sequences coding for secretion signals in lactic acid bacteria and novel signal peptides isolated from *Lactococcus* spp., and mutants of such signal peptides having enhanced efficiency.

TECHNICAL BACKGROUND AND PRIOR ART

The group of Gram-positive bacteria that are generally referred to as lactic acid bacteria including *Lactococcus* spp. such as *Lactococcus lactis, Lactobacillus* spp., *Streptococcus* spp., *Leuconostoc* spp. and *Oenococcus* spp. are commonly used in the manufacturing of food products and feedstuffs, e.g. as dairy starter cultures in the manufacturing of fermented milk products such as butter, cheese and yoghurt. *Lactococcus lactis* is a typical example of a Gram-positive bacterium used for the manufacturing of a wide range of fermented milk products.

Besides, lactic acid bacteria are currently used as recombinant host cells for the production of heterologous and homologous gene products such as pharmaceutically active products or enzymes. Among the emerging industrial applications for *L. lactis*, recent work by the inventors has focused on the production of heterologous proteins with a potential as vaccines, therapeutics or enzymes. The expression system used includes a strong regulated promoter and has allowed a high-level production of recombinant *Leuconostoc mesenteroides* β-galactosidase, LacLM (Madsen et al., 1999).

With the development of microorganisms as cell factories for the production of heterologous proteins, a number of genetic tools for improved gene expression have been established. These include strong promoters, high copy number vectors, optimised codon usage and improved production strains, and their use has resulted in an increase of production levels.

Using these optimised tools, secretion of heterologous proteins into the culture supernatant might represent a limiting step. Therefore, the molecular knowledge of protein secretion is also emerging as a subject of applied research. To facilitate downstream processing of recombinantly produced protein, secretion of the protein is generally desired. To achieve efficient secretion of heterologous gene products it is required that constructs are used in which the gene coding for the desired gene product is operably linked to a gene coding for an effective signal peptide that can be recognised by the signal peptidases of the host cell.

The process of secretion in bacteria includes events that occur just after translation of the mRNA, i.e. the subsequent recognition of the signal peptide (SP) in the nascent unfolded polypeptide chain by the Sec apparatus and cleavage by signal peptidase upon translocation through the cell membrane.

The Sec-dependent pathway is the best studied system for protein export. Although it is known that virtually all proteins exported via this mechanism require a SP, it is not clearly understood how the structure of the SP interacts with the different components of the secretion machinery in the cell. The recent characterization of a Sec-independent pathway that is conserved between *E. coli* and plants illustrates the fact that proteins are exported through a number of distinct pathways (Settles and Martienssen, 1998; Stephens 1995). The mechanisms involved normally require the presence of sequence motifs in the exported protein.

SPs are the N-terminal extensions present in Sec-dependent secreted proteins. The structure of a typical SP includes three distinct regions: (i) an N-terminal region that contains a number of positively charged amino acids, lysine and arginine; (ii) a central hydrophobic core and; (iii) a hydrophilic C-terminus that contains the sequence motif recognised by the signal peptidase (von Heijne 1990). Despite structural similarities, large sequence variation is observed between different SPs. This variation has recently been related to specific targeting of the secreted proteins (Martoglio and Dobberstein, 1998). Studies of secretion in *Escherichia coli* have shown the influence of the hydrophobic core region of SP on efficient processing. SPs with highly hydrophobic core regions supported a high rate of transport even when an altered N-terminal region with negative charge is used (Izard et al., 1996). PhoA has been used as a model protein for detailed secretion studies in this bacterium. The effect of the removal of helix-breaking residues (Gly or Pro) can be compensated by increased hydrophobicity (Izard et al., 1995). In competition experiments, two identical SPs were placed N-terminal to PhoA and the rate of utilization of either SP was shown to be dependent on small increases in the hydrophobicity of one of the SP (Chen et al., 1996). Moreover, it was shown that a reduced negative charge at the amino terminus resulted in a lower overall affinity for the transport pathway (Izard et al., 1996).

The characterisation of numerous extracellular proteins has allowed development of a method for the prediction of the presence and location of signal peptide cleavage sites in amino acid sequences from different organisms including Gram-positive and Gram-negative prokaryotes, and eukaryotes (Nielsen et al., 1997). The method involves a prediction of cleavage sites and a signal peptide/non-signal peptide prediction based on a combination of several artificial neural networks. The use of this method permits the preliminary design and analysis of SP derivatives prior to their construction and test in vivo.

Proteins that are targeted for secretion include a signal sequence or signal peptide (SP) at the N-terminus. SPs are recognised and cleaved by a leader or signal peptidase, a component of the secretion machinery of the cell, during translocation across the cell membrane (Martoglio and Dobberstein, 1998). SPs are normally 25 to over 35 amino acids (aa) in size in Gram-positive bacteria. SPs do not share sequence homology, but are often composed of an amino terminus that includes one or more basic aa, a central hydrophobic core of seven or more aa, and a hydrophilic carboxy terminus containing the motif that is recognized by signal peptidases (Martoglio and Dobberstein, 1998). A survey of available SPs from *L. lactis* suggested the use of the SP from Usp45, the major secreted lactococcal protein (van Asseldonk et al., 1990). This SP was reported to be functional in the secretion of several heterologous proteins in *L. lactis* (van Asseldonk et al., 1993).

Traditional strategies for the identification of SPs in *L. lactis* have followed the construction of genomic libraries in a vector carrying a promoterless reporter gene. In general, work in Gram-positive bacteria has involved the use of reporter genes with a demonstrated functionality for the identification of SPs in Gram-negative bacteria. These reporters include BlaM, the *E. coli* β-lactamase (Sibakov et al., 1991; Perez-Martinez et al., 1992). The use of BlaM for the identification of *L. lactis* SPs implied a limitation on the possibility of direct screening in *L. lactis* and this has been assumed to be due to differences in codon usage and protein folding requirements for BlaM (Pouquet et al., 1998). Therefore, primary screening of Gram-positive bacterial genomic libraries has up till now been carried out in *E. coli* and positive clones subsequently tested in *L. lactis* (Sibakov et al., 1991; Perez-Martinez et al., 1992) thereby imposing a tedious and labour consuming selection step for functionality in the primary host. A more appropriate secretion reporter, the extracellular β-amylase from *Bacillus licheniformis* has also been used in screening for lactococcal SPs, but following the same screening strategy (Perez-Martinez et al., 1992). These strategies resulted in the isolation of SPs of type I exclusively. Moreover, some of the functionality of the sequences identified was due to the presence of amino acid residues derived from the multiple cloning site in the vector. These amino acids matched the requirements for the C-terminal region of this type of SPs (Perez-Martinez et al., 1992).

However, it is desirable to dispose of a broad range of SPs in order to select, for specific purposes, such SPs that are suitable in a particular host cell or for the secretion of a particular gene product. A major objective of the present invention is therefore to provide a convenient method for direct isolation of lactic acid bacterial nucleotide sequences coding for signal peptides that are functional in a broad range of host cells including lactic acid bacterial cells, which method does not require an intermediate screening step in another species. A further objective of the invention is to provide a transposable element useful in the present method that permits to identify and locate, in a bacterial chromosome, sequences coding for SP. By using the novel method several novel lactococcal SPs were identified, isolated and improved by mutagenesis.

SUMMARY OF THE INVENTION

Accordingly, the invention pertains in a first aspect to a method of constructing a transposon derivative for identifying in a lactic acid bacterium a DNA sequence coding for a signal peptide (SP), the method comprising the steps of (i) selecting a DNA molecule comprising a transposon including between its left terminus (LR) and its right terminus (RR) a sequence comprising a promoterless promoter reporter gene and a ribosome binding site (RBS), (ii) deleting from said DNA molecule a region located between the LR and the promoterless reporter gene to obtain a modified DNA molecule that has retained its transposability and its RBS, (iii) inserting into the remaining region located between the LR and the promoterless reporter gene of the resulting modified DNA molecule a unique restriction site, and (iv) inserting into said unique restriction site a DNA sequence coding for a secretion reporter molecule, said DNA sequence coding for a reporter molecule is without a sequence coding for a SP, the thus obtained transposon derivative being without stop codons in-frame with the secretion reporter molecule thus permitting upon transposition translational fusions from upstream the LR.

In a further aspect there is provided a transposon derivative for the identification in a lactic acid bacterium of a DNA sequence coding for a signal peptide (SP), the molecule comprising the following elements: (i) a DNA molecule comprising a transposon element including between its left terminus (LR) and its right terminus (RR) a sequence comprising a promoterless promoter reporter gene and a ribosome binding site, the DNA molecule being without stop codons in the region upstream of the promoter reporter gene. (ii) a DNA sequence coding for a secretion reporter molecule, said DNA sequence is without a sequence coding for an SP.

In a still further aspect, the invention relates to a method of identifying in a lactic acid bacterium a DNA sequence coding for a signal peptide (SP), the method comprising the steps of (i) transforming a lactic acid bacterium with a transposon derivative as defined above and (ii) selecting from the transformed lactic acid bacterium, cells in which the promoterless promoter reporter gene is expressed and the gene product of the DNA sequence coding for a secretion reporter molecule is secreted.

In yet other aspects there are provided an isolated DNA molecule comprising at least part of a transposon derivative as defined herein and a DNA sequence coding for a signal peptide (SP) that is functional in a lactic acid bacterium and an isolated DNA sequence coding for a signal peptide that is derived from a molecule selected from the group consisting of SP10, SP13, SP307, SP310 and SP330 as described hereinbelow, and a derivative of any of said signal peptides having retained signal peptide functionality. It was found that such derivatives can have an enhanced secretion efficiency as compared to the corresponding wild type SPs.

Further aspects of the invention include: a recombinant plasmid comprising an isolated DNA molecule comprising at least part of a transposon derivative or an isolated DNA sequence according to the invention; a recombinant bacterium comprising a DNA sequence according to the invention; and use of such a bacterium for the production of a desired gene product.

DETAILED DISCLOSURE OF THE INVENTION

A major objective of the present invention is to provide a novel transposable element that permits the direct identification, i.e. without the use of an intermediate bacterial species, in the genome of a lactic acid bacterium of a sequence coding for a SP. Such an element is provided by the above method of constructing a transposon derivative for identifying in a lactic acid bacterium a DNA sequence coding for a signal peptide (SP).

In a first step of the method a DNA molecule is selected that comprises a transposon including between its left terminus (LR) and its right terminus (RR) a sequence comprising a promoterless promoter reporter gene and a ribosome binding site (RBS). In the present context, one such useful DNA molecule is one comprising the Tn917 transposon or a derivative hereof. A particularly useful Tn917 derivative is the plasmid pLTV1 that in addition to the Tn917 transposon comprises a promoterless lacZ gene and a ribosome-binding site (RBS).

From the selected basic transposable DNA molecule a region, located between the LR and the promoterless reporter gene, is deleted to obtain a modified DNA molecule that has retained its transposability and its RBS, followed by inserting a unique restriction site into the remaining region located between the LR and the promoterless reporter gene and inserting into said unique restriction site a DNA sequence coding for a secretion reporter molecule that does not include a sequence coding for a SP.

By deleting the region located between the LR and the promoterless reporter gene it is achieved that the thus obtained transposon derivative is without stop codons in-frame with the secretion reporter molecule permitting, upon transposition, translational fusions from upstream the LR.

Among secretion reporters that can be used in *L. lactis* and other lactic acid bacterial species, genes coding for nucleases are presently preferred, including the *Staphylococcus aureus* nuclease (Nuc), a naturally extracellular protein that has been shown to be useful in *L. lactis* as secretion reporter (Poquet et al., 1998). Nuc is suitable for the screening for SPs since the protein is inactive intracellularly and its structure is remarkably simple (it is a monomer, lacks disulfide bonds). Furthermore, the codon usage in the nuc gene is appropriate for high level expression in lactococci, and the plate assay for detection of secretion is not toxic, eliminating the need for replica plating.

In another aspect, the invention provides a novel transposon derivative molecule, which is useful in the above method for the identification in a lactic acid bacterium of a DNA sequence coding for a signal peptide (SP). Such a molecule comprises a first element in the form of a DNA molecule comprising a transposon element including between its left terminus (LR) and its right terminus (RR) a sequence comprising a promoterless promoter reporter gene and a ribosome-binding site. One example of a useful promoter reporter gene is the lacZ gene.

It is a significant feature of this first element that the DNA molecule is without stop codons in the region upstream of the promoter reporter gene that are in-frame with the secretion reporter molecule of the below second element, which permits, upon transposition of the transposon derivative, the expression of translational fusions from upstream the LR.

The transposon derivative molecule comprises, as a second element, a DNA sequence that codes for a secretion reporter molecule, said DNA sequence is without a sequence coding for a SP. In a presently preferred embodiment, the secretion reporter gene is a gene coding for a nuclease such as the nuc gene derived from *Staphylococcus aureus*.

In useful embodiments, the transposon derivative is derived from Tn917 or a derivative hereof including pLTV1. A particularly useful transposon derivative according to the invention is pTnNuc, the construction and function of which are described in details in the following examples. In addition to the above first and second elements, the transposon derivative may further comprise a selection marker, e.g. an antibiotic resistance gene or a mutation conferring auxotrophy against an essential nutrient component.

A major objective of the invention is to provide a method of identifying in a lactic acid bacterium a DNA sequence coding for a signal peptide (SP). The method comprises the steps of transforming a lactic acid bacterium with a transposon derivative molecule as described above and selecting from the transformed lactic acid bacterium, cells in which the promoterless promoter reporter gene is expressed and the gene product of the DNA sequence coding for a secretion reporter molecule is secreted.

It will be appreciated that an expression of the promoter reporter gene is an indication that the transposable element has been integrated into a gene of the lactic acid bacterial cell at a position where it is operably linked to a promoter in the chromosome of the cell. Simultaneous screening for expression of the promoterless reporter gene and the secretion reporter gene on media which are indicative for the fusion product of the promoter reporter gene and the secretion reporter gene permits the direct identification of clones comprising a sequence coding for a functional SP.

In accordance with the invention, the lactic acid bacterium, which is used in the above as a source for functional SPs, can be of any species belonging to the group of bacteria generally referred to as lactic acid bacteria. This group includes *Lactococcus* spp. such as *Lactococcus lactis*, *Lactobacillus* spp. including as examples *Lactobacillus acidophilus* and *Lactobacillus pantarum*, *Leuconostoc* spp. such as *Leuconostoc mesenteroides*, *Oenococcus* spp. and *Streptococcus* spp.

In preferred embodiments, the transposon derivative is transposed randomly or quasirandomly.

It will be appreciated that when clones comprising a sequence coding for a functional SP have been identified using the above method, such a sequence can be isolated in accordance with conventional techniques for isolating nucleotide sequences. Having isolated such a sequence it can, if desired, be inserted into homologous or heterologous species with the aim of improving or optimising the secretion of desired gene products.

Accordingly, the invention pertains in a further aspect to an isolated DNA molecule comprising at least part of a transposon derivative as defined above and a DNA sequence coding for a signal peptide (SP) that is functional in a lactic acid bacterium. In useful embodiments, such a DNA molecule comprises a sequence coding for a signal peptide comprising a signal peptidase I-recognition sequence or a signal peptidase II-recognition sequence. In this context, suitable DNA molecules include such molecules where the DNA sequence coding for a signal peptide is derived from a clone selected from the group consisting of SP10, SP307, SP310 and SP330 as described in the following examples, and a mutant thereof.

It has been found that it is possible to enhance the secretion efficiency of a desired gene product by operably linking the gene coding for the gene product to a mutant of a sequence coding for a naturally occurring SP. Such a mutation can be produced by conventional mutagenesis techniques such as mutagenesis by means of UV irradiation or by using chemical mutagens. However, site-directed mutagenesis has been found to be a convenient and effective means of producing SP mutants having improved functional characteristics. Such a mutagenesis may result in substitution, deletion or addition of one or more amino acid residue. In the following examples, a range of such mutated SPs are described, of which several show a higher secretion efficiency than the corresponding wild type SP. These mutants include those designated herein as 310mut1, 310mut2, 310mut3, 310mut4, 310mut5, 310mut6, 310mut7, 310mut8, 310mut10, 310mut11, 310mutA, 310mutB, 310mutC, 310mutA1, 310mutB1, 310mutD2, 310mutD7, 310mutE2, 310mutE11 and 310mutF2, respectively.

The invention also provides novel isolated DNA sequences coding for a signal peptide that are derived from a molecule selected from the group consisting of SP10, SP13, SP307, SP310 and SP330 as described herein, and a derivative of any of said signal peptides having retained signal peptide functionality, including DNA sequences derived from any of the above mutants. There are also provided recombinant plasmids comprising an isolated DNA molecule comprising at least part of a transposon derivative according to the invention or an isolated DNA sequence as described above. Such plasmids include a recombinant plasmid that is selected from the group consisting of Δ10::Nuc, Δ13::Nuc, Δ307::Nuc and Δ310::Nuc as described herein. In useful embodiments, the recombinant plasmid according to the invention comprises a regulatable promoter operably linked to the secretion reporter gene. The regulation of the promoter activity is preferably caused by growth condition factors for the host cell carrying the plasmid such as the growth temperature, the pH, the growth phase and changes of the nutrient composition of the medium occurring during growth of the host cell. In the present context, one useful promoter is the P170 promoter as described hereinbelow.

In a still further aspect, the invention pertains to a recombinant bacterium comprising a DNA sequence coding for a signal peptide that is derived from a molecule selected from SP10, SP13, SP310 and SP330, and a derivative of any of these SPs that has retained SP activity. In such a bacterium, this DNA sequence is preferably operably linked to a gene expressing a desired gene product whereby the gene product is secreted. Such a recombinant bacterium is any Gram-positive or Gram-negative bacterium that is used as host cell in the production of desired gene products. Typical examples of Gram-positive bacteria include lactic acid bacterial species, *Bacillus* spp. and *Streptomyces* species and examples of Gram-negative bacteria include as a typical example *E. coli*.

The invention will now be illustrated in the following non-limiting examples and the drawings wherein FIG. 1A illustrates the construction of pTnNuc, a secretion reporter tool in *L. lactis*. Details of the construction of TnNuc are described in Example 1. Plasmids are not drawn to scale and only relevant features are shown. Restriction sites. A: AalI; B: BsmI; E: EcoRV; N: NsrI; R: RsrII; S: SmaI. The pPRA plasmids contain the 3.1 EcoRV fragment from pLTV1 spanning from the coding region of the tet gene (open tet arrow) to within the lacZ gene (stripped lacZ arrow) and including the left repeat of Tn917 (filled LR box). This fragment (open LTV1 box) and the position of the LR (filled LR box) are shown in pPRA plasmids for clarity. The region deleted between the LR and lacZ is depicted as an open triangle in pPRA4B.

Figure 1B:
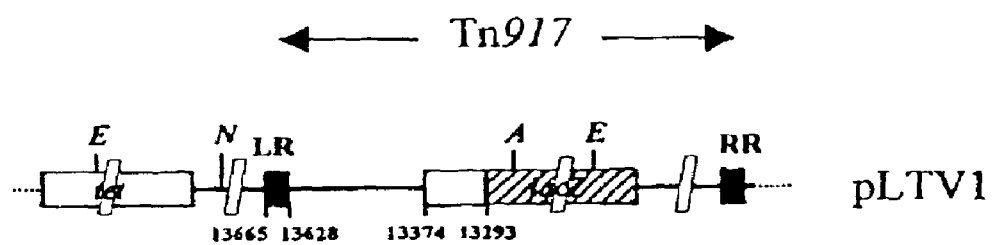
Figure 2:
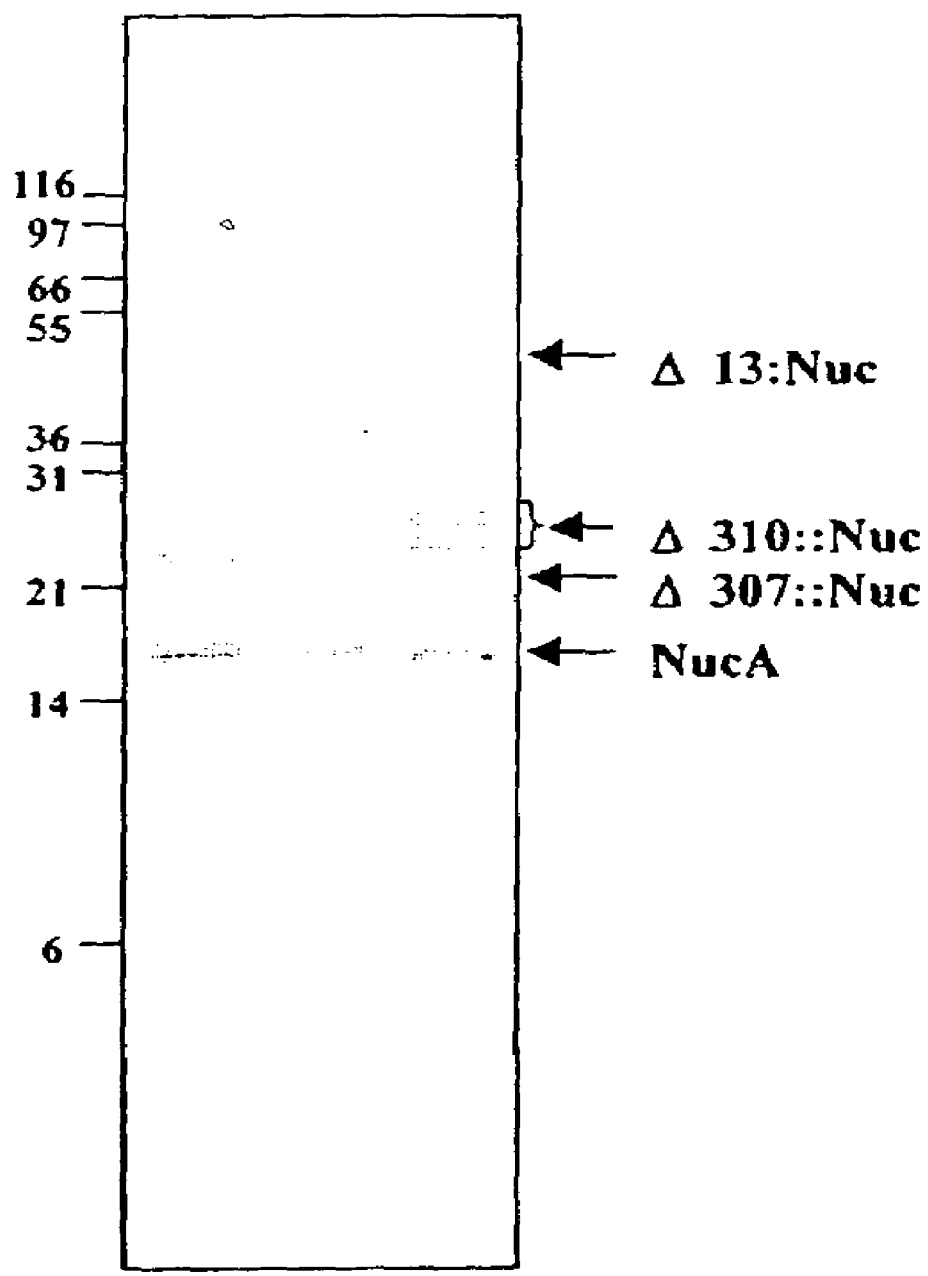
Figure 3:
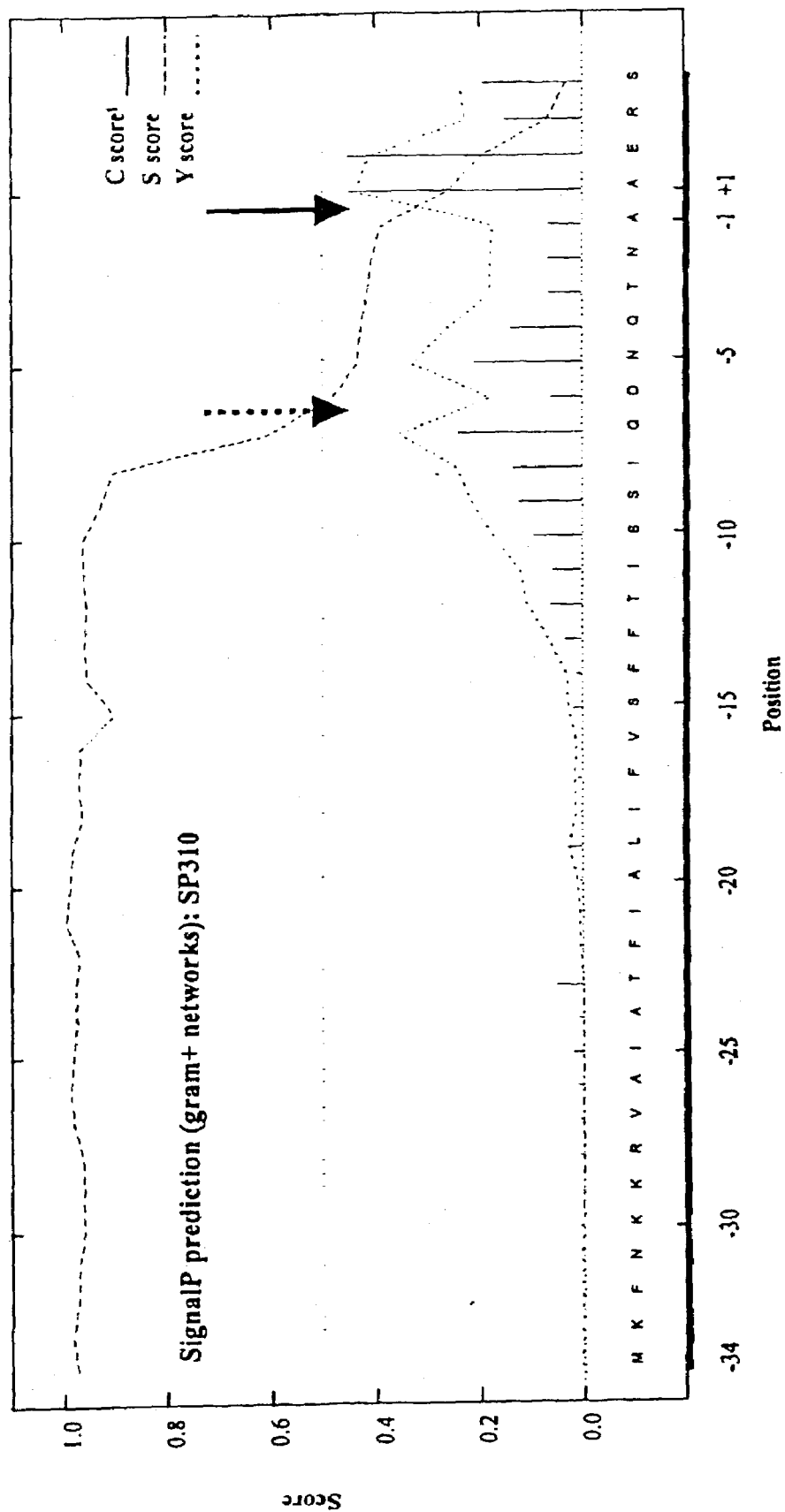
Figure 4:
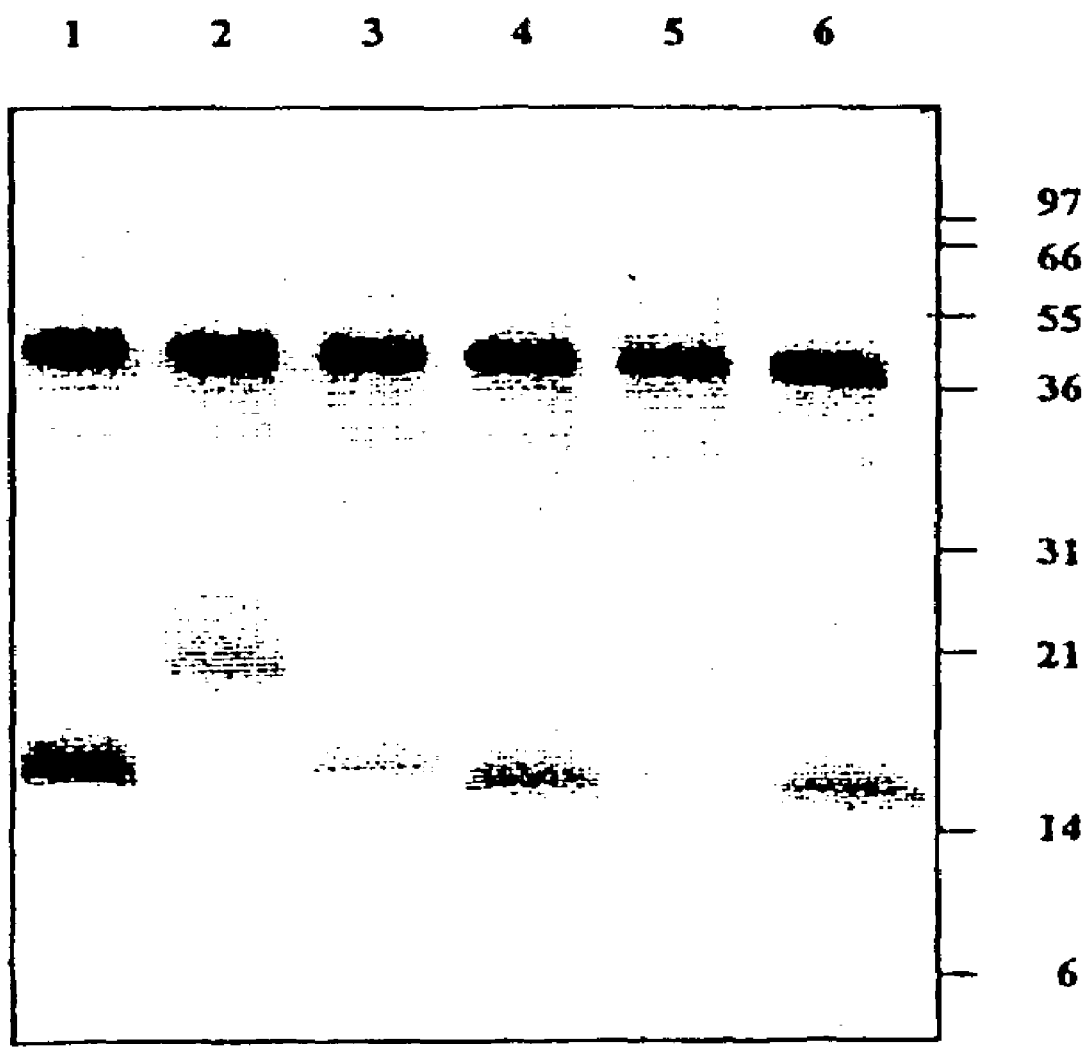

FIG. 1B illustrate details of the nt positions used in the deletion analysis of the Tn917 derivative in pLTV1 are indicated together with the functionality of the different pPRA5 derivatives in transposition;

FIG. 2. summarises an analysis of secretion efficiency for selected *L. lactis* SPs. Concentrated (20-fold) supernatants of strain PRA 157 (lane 1), PRA 158 (lane 2) and PRA159 (lane 3) were run on a 16% Tricine gel and Coomasie stained. The volume loaded represents the total protein content from 100 μl (PRA157 and PRA158) or 50 μl (PRA159) of culture supernatant. The migration of molecular weight markers in kDa is shown to the left. The position of NucA and the corresponding full length protein (Δ13::Nuc, Δ307::Nuc and Δ310::Nuc is shown to the right). A weaker band with similar migration to Δ13::Nuc and present in all strains corresponds to Usp45, the major secreted protein from *L. lactis* (van Asseldonk et at., 1990);

FIG. 3. is an overview of the site-directed mutagenesis strategy for SP310 and Nuclease secretion. The profile obtained from the analysis of the wild type SP310 (SP310) using SignalP is shown above. C, S and Y scores are the three parameters used in SignalP for the identification of a SP. The arrow indicates the suggested main processing site between residues Ala34–Ala35, sequence alterations are underlined; and FIG. 4 shows secreted nuclease yield in *L. lactis* strains containing an altered SP310. Supernatants from overnight cultures were concentrated about 50-fold by TCA-precipitation. A volume corresponding to 0.5 ml culture supernatant was run on a 14% SDS PAGE (Novex). Lane 1: strain PRA76 (Usp45SP-Nuc); lane 2: strain PRA159 (original construction with 60 aa from the SP310 sequence fused to the mature Nuc); lane 3: strain PRA162 (only the 35 aa of SP310 fused to Nuc); lane 4: strain PRA164 (310mut 2-Nuc); lane 5: strain PRA170 (310mutB-Nuc); lane 6: strain PRA250 (310mut6-Nuc); The migration of molecular weight markers is indicated to the left in kDa.

EXAMPLE 1

The Development of TnNuc and its Use for the Isolation of Novel Secretion Signals in *Lactococcus lactis*

Abbreviations: aa: amino acid(s); B.: *Bacillus*; bp: base pair; E.: *Escherichia coli*, Em: Erythromycin; L.: *Lactococcus*; LR: left repeat; nuc: Nuclease coding gene; Nuc: Nuclease protein; nt: nucleotide; S.: *Staphylococcus*; SP(s): signal peptide(s) or secretion signal; St.: *Streptococcus*

1.1. Abstract

The construction of a new Tn917-transposon derivative, termed TnNuc, which includes the *Staphylococcus aureus* nuclease gene (nuc) as a reporter for secretion is described. Transposition of TnNuc into the *L. lactis* chromosome permits the generation of fusions inframe with the nuc gene. TnNuc also includes lacZ, a reporter used for identification of relevant clones from the library, i.e. clones with Lac+ phenotype resulting from transposition of TnNuc into a functional gene on the *L. lactis* chromosome. The presence of a functional signal sequence at the upstream flanking region of the left repeat of the transposed element results in the detection of nuclease activity using a sensitive plate assay. TnNuc was used for the identification of novel secretion signals from *L. lactis*. The sequences identified included known and unknown lactococcal secreted proteins containing either a signal peptidase-I recognition sequence or a peptidase-II recognition sequence. In one case, the gene identified codes for a transmembrane protein. The identified sequences were used to study functionality when located in a plasmid under the control of the pH and growth phase-dependent promoter P170 (Madsen et al. 1999). In all cases concurrent secretion of nuclease was observed during induction of P170 in a chemostat.

1.2. Materials and Methods (i) Strains and Growth Conditions

*Escherichia coli* K-12 strain DH10B (Grant et al., 1990) grown in LB supplemented, if appropriate, with 100 μg/ml ampicillin or 200 μg/ml erythromycin (Em), at 37° C. was used for cloning purposes, rescue of plasmid DNA and propagation of plasmid DNA. *Lactococcus lactis cremoris* strain MG1614 (Gasson 1983) was used in experiments involving construction of transposon insertions, screening, analysis of transposon insertions and plasmid rescue of DNA adjacent to site of insertion. *L. lactis* subsp. cremoris strain MG1614 (Gasson 1983) were used for analysis of isolated translocation signals. *L. lactis* strains were grown in GM17 or ArgM17 (Israelsen et at., 1995) at 30° C. supplemented, if appropriate, with 1 μg/ml erythromycin (GM17Em or ArgM17Em). In fermentor experiments, a defined medium, 3×SAIV (Jensen and Hammer, 1993) was used and pH was maintained using KOH.

Transformation of bacteria was performed by electroporation, according to published procedures for *E. coli* (Sambrook et al., 1989) and *L. lactis* (Holo and Nes 1959), respectively.

(ii) Plasmid and TnNuc Construction

The strategy for the construction and analysis of deletion derivatives of Tn917-LTV1 (Camilli et al., 1990) is illustrated in FIG. 1. The 3.1 kb EcoRV fragment from pLTV1, spanning from the 3' end of the lacZ gene to the coding region of the tet gene (positions 12208 to 15335) was subcloned into EcoRV-digested pBluescript SK-(Stratagene), resulting in pPRA2. Plasmid DNA from pPRA2 was used as a template for PCR using primer PSS1b (5'-CGATG AATGCCGGACCGAAT TGATACACTA ATGCTTTTAT ATAGGG-3'(SEQ ID NO:1) containing restriction site for Bsml (underlined) and RsrII (italics), respectively; position 13374–13348 in pLTV1) and primer PSS14 (5'-GTG-TAGTCGG TT-TATGCAGC-3'(SEQ ID NO:2); position 12672–12691 in the lacZ gene). The amplified 720-bp fragment was digested with Bsml and AatII (unique site in the 3.1 kb pLTV1 fragment in pPRA2, FIG. 1) and cloned into Bsml and AatII-digested pPRA2, resulting in pPRA3. Four different PCR products (designated 2A to 2D) were amplified using pPRA2 DNA as template. PCR was carried out using primer PSS3 (5'-CACACATACC AATACATGC-3'(SEQ ID NO:3); position 14391–14373 in pLTV1, see FIG. 1) in combination with the following primers containing a unique RsrII site (italics): (i) for 2A, primer PSS4 (5'-GCATCGGTCC GTAGGCGCTC GGGACCCC-3' (SEQ ID NO:4). position 13665 to 13647 in pLTV1); (ii) for 2B, primer PSS6 (5'-GCATCGGTCC GTTCTTATCG ATA-CAAATTC CTCG-3' (SEQ ID NO:5), position 13648 to 13626 in pLTV1); (iii) for 2 C, primer PSS8 (5'-GCATCG-GTCC GAAATTTTTA AATCTATTTC TTATC-3' (SEQ ID NO:6), position 13633 to 13608 in pLTV1) and (iv) for 2D, primer PSS10 (5'-GCATCGGTCC GTAAATGTAC AAAATAACAG CGAAAT-3' (SEQ ID NO:7), position 13613 to 13589 in pLTV1).

Fragments 2A to 2D were digested with RsrII and NsiI (a unique NsiI site in the 3.1 kb EcoRV fragment from pLTV1, see FIG. 1) and cloned into likewise digested pPRA3, resulting in pPRA4A to pPRA4D, respectively. pPRA4A to pPRA4D were digested with EcoRV and the 2.8–2.9 kb inserts were cloned into EcoRV-digested pLTV1 to replace the original 3.1 kb fragment, resulting in plasmids pPRA5A tp pPRA5D (FIG. 1).

pPRA5B was chosen to construct TnNuc. Using pBS::Nuc (Le Loir et al., 1997) as DNA template and primers PSSnuc1 (5'-GCATCGGACC GTCACAAACA GATAACGGCG-3' (SEQ ID NO:8), RsrII site in italics) and PSSnuc2 (GCATCGGTCC GCATTATTGA CCTGAAT-CAG-3' (SEQ ID NO:9), RsrII site in italics), a 531 bp fragment was obtained. Digestion with RsrII and subsequent ligation into likewise treated pPRA5B was carried out and resulted in pTnNuc. The nuc fragment codes for the NucB form of the protein (Poquet et al., 1998).

Transposon insertions were made by transforming *L. lactis* with the vector carrying the Tn917 derivative and growing these with erythromycin selection. Plates with transformants were either replica plated on X-gal plates as described by Israelsen et al. (1995) followed by Nuclease plate (Nuc) assays of LacZ+-klones or a library of transposon insertions was generated by plating transformed *L. lactis* with high density an 140 mm petri dishes each with 200 ml SGM17 agar suplemented with 1 µg/ml Em. Plates were incubated 4 days at 30° C. and clones were pooled by resuspending colonies in GM17Em and 17% glycerol. The constructed library was frozen in small aliquots. An aliquot was subsequently plated at a density of c. 500 cfu/plate on either GM17Em or ArgM 17Em. Nuc assays were then performed on colonies to identify Nuc secreting clones.

For the analysis of the functionality of the isolated SPs on plasmid, pAM J206 was used. pAMJ206 contains the *L. lactis* regulated promoter P170 (Madsen et al., 1999) located upstream of the ribosome binding site (RBS) from pAK80 (Israelsen et al., 1995). Unique BglII and SaII sites are conveniently located just downstream of the RBS. A PCR fragment was obtained from pBS:Nuc (Le Loir et al., 1997) using primers Nuc1 and Nuc2 (respectively, 5'-GGAA-GATCTT CACAAACAGA TAACGGC-3' (SEQ ID NO:10) and 5'-ACGCGTCGAC GAATTCGATC TAAAATTAT AAAAGTGCC-3' (SEQ ID NO:11) restriction sites in italics), digested with BglII and SalI and ligated into pAMJ206, resulting in pΔSPNuc. This plasmid was used for the construction of plasmid pPRA157, pPRA158 and pPRA159 as follows. In pPRA157, a PCR fragment was amplified from chromosomal DNA of *L. lactis* MG 1614 using primer PSScluA-A and PSScluA-B (respectively, 5'-GCATC-CCGGG TCTAGATTAGGGTAACTTTGAAAGGATATTCCTCatg -AAA AAAACATTGA GAGACCAGTTACTTG-3' (SEQ ID NO:12) and 5'-GCATAGATCT ACTCCAACTA TCAC-CTGTTG CATTTGCTC-3' (SEQ ID NO:13), restriction sites, SmaI and BglII in italics, the sequence from the expression vector pAMJ203 is underlined and the cluA gene ATG start codon is shown in lower case). This fragment spans from the start codon of the cluA gene to a position 1200 bp downstream. At this position, insertion of TnNuc was observed in clone SP13. This fragment was cloned into SmaI-BglII digested pΔSPNuc resulting in an in-frame fusion protein CluA::Nuc containing just two aa differences (Arg-Ser, derived from the cloning sites) to the protein produced in SP13.

Construction of pPRA158 and pPRA159 was carried out similarly, but cloning a PCR fragment corresponding to the first 120 bp of the coding region for the genes inactivated by TnNuc insertion in clone SP307 (fragment amplified using primers PSS307-A, 5'-GCATCCCGGG TCTAGATTAG GGTAACTTTG AAAGGATATT CCTCATGAAT AAAT-CAAAAA TTATTGCTTT CTCTGC-3' (SEQ ID NO:14) and PSS307-B, 5'-GCATAGATCT ATCAATGGAA TTAA-CATCAG CTGCCATGC-3' (SEQ ID BO15), respectively. SmaI and BglII sites in italics) and SP310 (fragment amplified using primers PSS310-A, 5'-GCATCCCGGG TCTA-GATTAG GGTAACTTTG AAAGGATATT CCTCAT-GAAA TTTATAAAAA AAAGAGTTGC AATAGCC-3' (SEQ ID NO:16) and PSS310-B, 5'-GCATAGATCT GTTATCATTA AAATCACTCC GATTAAGAG-3' (SEQ ID NO:17), respectively, SmaI and BglII sites in italics), respectively in pΔSPNuc.

Additionally, strain AMJ627 was constructed by cloning a PCR fragment containing the N-terminal 29 aa that include the SP from Usp45 (SP$_{usp}$, amplified using primers Usp1 (5'-TAGTAGGATC CCGGGTCTAG ATTAGGGTAA CTTTGAAAGG ATATTCCTCatg AAAAAAAA GAT-TATCTCAGC-3' (SEQ ID NO:18), SmaI site in italics, usp45 ATG start codon in lower case) and Usp2 (5'-ACGCGTCGAC CTGCAGAGAT CTTGTGTCAG CGTAAACACC-3' (SEQ ID NO:19), BglII site in italics) into SmaI-BglI-digested pΔSPNuc. All plasmid constructions were confirmed by sequencing the relevant regions.

(iii) Nuclease Assay

Nuclease assay on plates was performed by the colony overlay method as described by Lachica et al., (1971), with the following modifications: 0.1% sonicated herring sperm DNA and 40 µM $CaCl_2$ was used in overlay and 1% agar was substituted with 0.6% agarose. Colonies were grown on GM17Em, ArgM17Em or LBEm plates with 0.3% glucose. The plates were incubated for 30 minutes to 6 h at 37° C. after solidification of overlay. Nuclease-secreting colonies developed as clear orange zone on a blue-green background.

(iv) Insertional Mutagenesis with Tn917 and Derivatives

Transposon insertion experiments were performed by transforming L. lactis with the vector carrying the Tn917 derivative and growing these with erythromycin selection. Primary transformants were replica plated on X-gal plates as decribed by Israelsen et al., (1995) followed by Nuclease plate assays of LacZ⁺-clones. Alternatively, a library of transposon insertions was generated by plating transformed L. lactis with high density on 140 mm petri dishes each with 200 ml SGM17 supplemented with 1 µg/ml Em Plates were incubated 4 days at 30° C. and clones were pooled by resuspending colonies in GM17Em and 17% glycerol. The constructed library was frozen in small aliquots. Aliquots were subsequently thawed and plated at a density of c. 500 cfu/plate on either GM17 or ArgM17 supplemented with Em. Plate assay was then performed on colonies to identify clones secreting nuclease.

(v) Pulsed Field Gel Electrophoresis

PFGE of SmaI-digested chromosomal DNA from L. lactis clones with integrated transposons was carried out as described (Israelsen and Hansen, 1993) to test the random distribution of TnNuc.

(vi) Plasmid Rescue

DNA from regions flanking the integrated Tnnuc transposon was characterised as follows. For the DNA region flanking the transposon LR, chromosomal DNA (2 µg) was digested with EcoRI, religated in a large volume (200 µl) to favour intramolecular ligation and transformed into E. coli DH10B. For the DNA region adjacent to the RR, chromosomal DNA was digested with either MluI or BsrWI before religation and transformation of E. coli DH10B.

(vii) Protein Characterization

Alternative culture supernatants were concentrated 20- to 30-fold using the Phenol-Ether procedure (Sauvé et al., 1995). Samples were run on 16% Tricine gels (Novex), according to the manufacturer. The gels were stained overnight using the colloidal Coomasie staining kit (Novex). The Mark 12 Wide Range Standard was used to estimate molecular sizes.

(viii) DNA Sequencing and Computer Analysis

Plasmid constructions and rescued plasmid DNA were sequenced using a Thermo Sequenase fluorescent labelled primer cycle sequencing kit (Amersham), Cy5-labelled primers and an ALFexpress DNA Sequencer (Pharmacia Biotech). DNA sequence data were analysed using the Wisconsin package from the Genetics Computer Group, Inc. Possible secretion signals were analyzed using the SignalP WWW server (Nielsen et at. 1997).

(ix) Fermentation

Fermentation experiments were carried out using bench top fermentors (Applikon) containing 1 liter of medium and set to operate at 30° C. and to maintain pH above 5.2.

1.3. Results (i) Identification of the Minimal Region Required for Transposition of Tn917 in Lactococcus lactis.

Transposition of the Tn917 derivative included in pLTV1 was demonstrated during the search for regulated promoters in L. lactis (Israelsen et al., 1995). This derivative contains a promoterless lacZ gene at the transposon left terminus and a ribosome binding site derived from the Bacillus subtilis spoVG gene. The SpoVG::lacZ sequence is inserted 278 bp from the end of Tn917, at a position where this insertion does not abolish transposition (Youngman, 1987). In order to develop a transposon-based screening tool for the identification of secretion signals from L. lactis, a reporter gene encoding a secreted protein must be inserted at the left terminus of the element, to allow the generation of in-frame fusions with genes encoding secreted proteins upon transposition. This requires a short distance from the left terminus of Tn917 together with the avoidance of stop codons that would prevent in-frame fusions with the reporter gene. Plasmids pPRA5A to pPRA5D were constructed as derivatives of pLTV1, each containing a small deletion that spans from a position within (pPRA5A) or adjacent to (pPRA5B to pPRA5D) the LR of Tn917 to the region just upstream of spoVG::lacZ (FIG. 1). A unique RsrII site was introduced in all derivatives upon deletion. L. lactis MG1614 was transformed using pLTV1 and pPRA5A-D. Transformants were grown through four rounds of replica plating in GM17Em plates. A large number of the initial transformants ceased to grow during replica plating. These corresponded presumably to isolates containing a poorly free replicating plasmid that was lost during subsequent growth on plates, rendering them Em-sensitive. Stable Em-resistant clones represent transposition of the Tn917 derivative into the L. lactis chromosome, although the possibility of integration of the plasmid carrying the transposon cannot be excluded in a fraction of the clones (Israelsen et al., 1995). Transformation of L. lactis MG1614 with pLTV1, pPRA5B, pPRA5C and pPRA5D resulted in a similar frequency of stable transformants. However, no stable transformants were obtained using pPRA5A. The Tn917 derivative in pPRA5A contains a partial deletion of the LR of the element. Alteration of this structural feature may be responsible for the observed lack of transposition in L. lactis. Sequence integrity in this region is required to delimit the boundaries of the element and high sequence homology is observed among Tn3-related elements like Tn917 (Sherrat et al., 1989).

In L. lactis MG1614, transformation with pLTV1 resulted in about 15% blue colonies among the stable Em-resistant clones on plates containing X-gal (Israelsen et al., 1995). Blue colonies result from Tn917 transposition downstream of a promoter in the L. lactis chromosome. No significant differences in the frequency of blue clones were observed with pPRA5B, pPRA5C or pPRA5D, compared to pLTV1 (data not shown) indicating that these derivatives were functional in L. lactis.

Since pPRA5B included the largest deletion and retained functionality, it was chosen to clone a secretion reporter, the S. aureus nuc gene.

(ii) Construction of TnNuc, a Tool for the Identification of Signal Peptides in L. lactis.

A PCR fragment including the entire nuc coding region downstream of the SP (see section 2.2) was cloned into the unique RsrII site of pPRA5B, resulting in pTnNuc (FIG. 1). In this construction, stop codons in-frame with the nuc gene are avoided allowing translational fusions from upstream the LR. The new transposon, named TnNuc, was used for the construction of a collection of mutants in L. lactis MG1614. TnNuc retains the original lacZ coding region and ribosome binding site. This additional feature of TnNuc provides a phenotypic trait (Lac+) to reveal the presence of promoter activity from sequences upstream of the LR upon transposition, regardless of the gene function. Thus, primary screening for blue colonies identifies L. lactis clones where true transposition occurs and where transcription into TnNuc occurs. Among them, a proportion of clones is expected to contain TnNuc adjacent to the 5' end of a gene encoding a secreted protein.

(iii) Construction and Screening of a Collection of TnNuc Integrants

Two independent transformation experiments of L. lactis MG1614 were carried out with pTnNuc. Since identification of a functional signal peptide requires both an active promoter and a gene encoding a secreted protein, initial screening focused on transposition events leading to expression of lacZ, excluding integration events not resulting in a fusion with a promoter in the correct orientation. In the first experiment, 147 Lac+ clones were isolated and assayed for nuclease secretion using the plate overlay assay. A number of clones that formed dark blue colonies on X-gal plates showed weak Nuc activity on plates. These clones represented transposition of TnNuc into a strongly expressed gene, and the low level of Nuc on plates might be the result of limited cell lysis and not actual secretion. Twelve clones showing a weak Lac+ phenotype and a low level of Nuc simultaneously were selected for further analysis, since in these cases true secretion of Nuc was more conceivable.

In the second type of experiments, an improved procedure was devised to reduce the elaborate and sequential screening mentioned above and to allow for the recovery of clones that would be lost during replica plating of primary integrants due to limiting promoter activity resulting in white colonies on X-gal plates. In this procedure, primary transformants were plated on SGM15Em plates and incubated for 4 days. This long incubation served the purpose of selection for true and stable Em-resistant integrants. Colonies were pooled and stored as a library that contained approximately $10^4$ independent transposants. Subsequent analysis of the library was carried out using the Nuc assay on plates. Nuc+ clones were then tested for LacZ activity. Out of 108 Nuc+ clones obtained, 20 clones showing either (i) a strong Nuc+ phenotype or (ii) a weak Nuc+ together with a weak Lac+ phenotype were selected for further analysis. These latter clones were assumed to include a TnNuc integration into a functional L. lactis gene.

In order to study the distribution of TnNuc in L. lactis chromosome, PFGE was carried out on SmaI-digested chromosomal DNA from 49 independent LacZ+ clones. The presence of TnNuc introduces two adjacent SmaI sites, included in the TnNuc sequence (FIG. 1), in the L. lactis chromosome. Thus, the disappearance of a single SmaI fragment from the PFGE profile of L. lactis MG1363 and the presence of two novel SmaI bands demonstrate the presence of TnNuc. Among the clones examined, 35 showed the presence of TnNuc in the largest, 600 kb SmaI chromosomal fragment. This frequency (71%) is consistent with the previously reported transposition frequency (60%) of a similar Tn917 system, TV32, into the same chromosomal region in L. lactis MG 1614 (Israelsen and Hansen, 1993). Two clones had one or two copies of TnNuc, respectively, in the 310 kb SmaI chromosomal fragment. TnNuc transposition into the 280 kb, 140 kb and 120 kb SmaI chromosomal fragments was observed for 3, 2 and 2 clones, respectively. For the remaining 6 clones, no apparent change in the PFGE profile was detected. Insertion of TnNuc in one of the smaller SmaI fragments is assumed since size change for these fragments would not be detected under the conditions used for PFGE (Israelsen and Hansen, 1993). These results confirmed the quasi-random distribution of TnNuc transposition in L. lactis.

(iv) Sequence Analysis of L. lactis Genes Coding for Secreted Proteins.

All 32 clones obtained showing a positive Nuc+/Lac+ phenotype were used in plasmid rescue experiments to characterize the genes affected by TnNuc transposition. In two cases, plasmid rescue in E. coli did not yield any transformants and the corresponding clones were not analysed further. Chromosomal DNA (300 to 400 bp) flanking the LR of TnNuc was sequenced on the rescued plasmids. In two cases, the sequence obtained corresponded to pTnNuc. Integration of pTnNuc but not transposition may have occurred in these L. lactis clones. For the remaining 28 clones, a sequence from the L. lactis chromosome was identified adjacent to the LR of TnNuc, representing true transposition events. DNA analysis revealed the presence of stop codons in the sequence just upstream of the TnNuc insertion, in-frame with the nuc gene in 10 clones. Among the remaining 18 clones, SP13 and SP36 included a TnNuc insertion in the cluA gene. CluA is a transmembrane protein involved in cell aggregation between donor and recipient bacteria during lactococcal conjugation (Godon et al., 1994). CluA has indeed a typical signal peptide, target for the signal peptidase I (Table 1). Nine clones were identified which contained a TnNuc insertion at 5 different positions within the same gene. This gene encodes a putative protein containing a signal peptide. A representative cone from this group, SP310, showed strong Nuc activity and low LacZ activity, indicating an effective signal sequence responsible for the secreted Nuc.

TABLE 1

Analysis of expression and secretion of selected TnNuc integrants. Homology search and type of signal peptide.

| Clone | No. isolated[1] | Nuc activity[2] | LacZ activity[3] | Protein or putative homologue | Signal Peptide Type[4] |
|---|---|---|---|---|---|
| SP10 | 1 (1) | + | +++ | PA243[5], unknown | I |
| SP11 | 2 (2) | +++ | ++ | Unknown | — |
| SP13 | 2 (2) | + | + | CluA (Godon et al. 1994) | I |
| SP240 | 1 (1) | ++ | + | DexB[6] | ND |
| SP307 | 1 (1) | +++ | +++ | Hyaluronan synthase[7] | II |
| SP310 | 9 (5) | ++ | ++ | Unknown | I |
| SP323 | 1 (1) | + | + | Membrane transporter[8] | ND |
| SP330 | 1 (1) | + | + | Unknown | — |

[1]The number of independent clones with a TnNuc insertion at the same locus is shown. Also the number of different locations within the target gene are given in brackets.
[2]Nuc activity was scored on plates using the overlay assay (see section 2.3).
[3]LacZ activity was scored on plates containing X-gal.
[4]Signal peptide analysis using the SignalP neural network (Nielsen et al., 1997); I: signal peptide type I; II: signal peptide type II (lipoprotein).
[5]Identical gene interrupted than in the previously isolated transposon integrant PA243 (Israelsen et al., 1995)
[6]Streptococcus mutans dexB. encodes an exoglycosylase involved n the metabolism of extracellular starch (Whiting et al., 1993).
[7]Hyaluronan synthase (HAS) from Streptococcus equisimilus (Ashbaugh et al., 1998).
[8]Homology to cation transporter proteins from E. coli.
ND: Sequence not available for the 5' end of the relevant gene.

Clone SP10 contained TnNuc insertion in a chromosomal locus adjacent to the thr operon that was previously identified during the search for regulated lactococcal promoters using pLTV1 (Madsen et al., 1996). SP10 showed strong promoter activity (LacZ), as it was reported for the pLTV1 integrant in the same locus, PA234 (Madsen et al., 1996). The protein encoded contained a putative signal peptide (Table 1).

Clone SP307 harboured a TnNuc insertion in a gene encoding a homologue of the streptococcal hyaluronase synthase (HAS), involved in capsule synthesis (Ashbaugh et al., 1998). A lipoprotein signal peptide (von Hejne, 1989)) is present at the N-terminus of the encoded protein (Table 1).

Analysis of clone SP11 and SP25 revealed an insertion of TnNuc at two different positions, 103 and 49 bp respectively from the ATG start codon of the disrupted gene. For SP25, the short sequence is not sufficiently long to conform to a SP. However, a favourable ratio between Nuc and LacZ activity was observed from both SP11 and SP25 (Table 1). The observed nuclease activity may be due to partial processing and secretion of the Nuc fusion protein. Alternatively, the inactivated gene may be responsible for a component of the secretion machinery or the cell membrane, leading to increased secretion or protein leakage.

In two clones, SP240 and SP330, no SP was identified in the targeted gene. For SP240, a database search identified significant homology to the St. mutans dexB gene. dexB encodes an exoglycosylase involved in the degradation of extracellular starch (Whiting et al., 1993). Interestingly, no SP is found in DexB (Table 1). The mechanism underlying the observed Nuc secretion in SP240 and SP330 remains unclear.

Finally a gene encoding a membrane protein was the insertion target in clone SP323. The putative protein showed homology to Mg2+ transporters of E. coli (Table 1).

(v) Functional Analysis of Selected Secretion Signals on a Multicopy Plasmid in L. lactis.

Four SPs representing sequences from known (SP13) and previously unknown genes (SP10, SP307 and SP310) and belonging to SPs recognized by signal peptidase I or II, were chosen for further analysis. To analyse secretion efficiency for the fusion partners identified with TnNuc in the wild type background, plasmid constructions were carried out to clone the minimal region (i.e., the closest position of insertion to the corresponding ATG start codon, see section 2.2). Preliminary results showed that a CluA-Nuc protein fusion carrying an N-terminal CluA region including the first 60–150 aa did not yield detectable amounts of secreted Nuc (data not shown). Therefore, a region including the N-terminal 400 aa of CluA corresponding to the closest position of TnNuc insertion to the 5' end of cluA identified herein was used for comparison (SP13).

For all other SPs, a 60 aa N-terminal region of the protein (SP10, SP307 and SP310) was introduced as a protein fusion with Nuc (hereafter called Δ10::Nuc, Δ13::Nuc, Δ307::Nuc and Δ310::Nuc, respectively), resulting in strain PRA156 (Δ10::Nuc), PRA157 (Δ13::Nuc), PRA158 (Δ307::Nuc) and PRA159 (Δ310::Nuc). The Nuc fragment used in this study corresponds to the NucB form of the protein. This form is further processed into a 19-to-21 aa shorter form, NucA (Pouquet et al., 1998). Strains PRA156 to PRA159 include a pH and growth-phase dependent promoter, P170, for regulated expression (Madsen et al., 1999). P170-driven expression occurs during transition to stationary phase, when the growth medium is kept at pH-6.5. Fermentor experiments were carried out using the above strains, and samples were taken at the onset of the stationary phase where maximum production levels have been obtained (Madsen et al., 1999). Initial measurements showed only background Nuc activity levels in culture supernatants of PRA156. This strain was therefore not analysed further.

Concentrated culture supernatants from PRA157, PRA158 and PRA159 were used to run SDS-PAGE. As shown, secretion of NucA was observed in all three strains (a 19-kDa band in lanes 1–3, FIG. 2). An additional band that corresponded in size to the full-length fusion protein was identified in PRA157 (a 42-kDa band) and PRA158 (a 22-kDa band; FIG. 2). In strain PRA159, two additional products of similar size (approximately 23 kDa) were detected, suggesting alternative processing sites of the SP in SP310). This possibility was supported by the identification of two putative processing sites of the primary aa sequence, at positions 27 and 34 from the initial Met, using SignalP. Overall, the secretion efficiency was highest for PRA159 (Δ310::Nuc) and lowest for PRA157 (ΔCluA::Nuc). The samples were used for measurement of Nuc activity (Table 2).

As a comparison, strain AMJ627 was used. AMJ627 harbours a construction similar to the above, and that includes the full SP from Usp45 fused to Nuc ($SP_{Usp}$::Nuc; see section 2.2). The values obtained confirmed the efficiency of the SP from Usp45 in secretion. The SP used in PRA159 (Δ310::Nuc) secreted 67 mg/L Nuc, or about 60% compared to $SP_{Usp}$. Activity levels were lower for PRA158 (31%) and PRA157 (6%).

TABLE 2

Nuclease activity in culture supernatants of selected clones.

| Strain (Fusion protein)[1] | Nuc activity | |
|---|---|---|
| | Total (mg/L) | mg/L × $OD_{600}$ |
| PRA157 (ΔCluA::Nuc) | 6.5 | 2.3 |
| PRA158 (Δ307::Nuc) | 34.1 | 10.0 |
| PRA159 (Δ310::Nuc) | 67.0 | 24.8 |
| AMJ627 ($SP_{Usp}$::Nuc) | 108.4 | 40.4 |

Stationary phase culture supernatants from fermentor experiments were used.
[1]See section 2.2 for construction details

EXAMPLE 2

Molecular Characterization and Engineering of SP310, a Signal Peptide From Lactococcus lactis 2.1 Abstract Among the signal peptides (SP) identified in Example 1, SP310 showed the highest level of secretion. However, the levels obtained were lower than those obtained using the signal peptide of Usp45 (SPUSP), the major secreted lactococcal protein. In this example is describes a site-directed mutagenesis approach for SP310 designed to improve secretion levels and to study the requirements for Sec-dependent secretion in L. lactis. One of the mutants analyzed, SP310mut2, showed a secretion level similar to SPUSP, yielding more than 150 mg/L Staphylococcus aureus Nuclease (Nuc) in fermentor. This represents a 45% improvement with respect to the wild type SP310 sequence. The analysis of Nuc secretion in the mutants allowed the establishment of some of the requirements for efficient secretion in L. lactis. Common features for the L. lactis Sec-dependent secretion pathway differ from the features reported for *Escherichia coli*.

2.2. Materials and Methods (i) Strains and Growth Conditions

*Escherichia coli* K-12 strain DH10B grown in LB or TB supplemented, if appropriate, with 100 μg/ml ampicillin or 200 μg/ml erythromycin (Em) at 37° C. was used for cloning purposes, rescue of plasmid DNA and propagation of plasmid DNA. *Lactococcus lactis cremoris* strain MG1363 (Gasson 1983) was used for analysis of SP. *L. lactis* strains were grown in GM17 (Israelsen et al., 1995) at 30° C. Supplemented, if appropriate, with 1 μg/ml erythromycin (GM17Em or ArgM17Em). In fermentor experiments, a defined medium, SAIV (Jensen and Hammer, 1993) was used and pH was maintained using HCl or NaOH. Transformation of bacteria was performed by electroporation, according to published procedures for *E. coli* (Sambrook et al., 1989) and *L. lactis* (Holo and Nes 1989), respectively.

(ii) Site-Directed Mutagenesis of SP310 and Plasmid Constructions

Primers PSS310-A (5'-GCATCCCGGG TCTAGATTAG GGTAACTTTG AAAGGATATT CCTCATGAAA TTT-TAATAAAA AAAGAGTTGC AATAGCC-3' (SEQ ID NO:20), SmaI site in italics) and PSS310-B0 (5'-CTATTG-GTTT GATTACGTCG GCTTTCTAGA TACG-3' (SEQ ID NO:21), BglII site in italics) were used to amplify the wild type SP310 sequence (hereafter designated SP310) using pPRA159 DNA as template. The amplified fragment was digested with SmaI and BglII, purified from agarose gels and cloned.

For the construction of 310mut1, PSS310-A and PSS310-B1 (5'-GGTTCTATTG GTTCGATTAC GTCGGCTTTC TAGATACG-3' (SEQ ID NO:22), BglII site in italics, mutation underlined) were used. PSS310-A and PSS310-B2 (5'-GTTATAGTAG TTAGGTTCTA CGAGTT - - - CGTCGGCTTTCTAGATACG-3' (SEQ ID NO:23), BglII site in italics, mutations underlined and deletion shown as lines) were used to obtain 310mut2.

310mut3 was produced by using PSS310-A and PSS310B3 (5'-CTATAAACAT TCAAAAAAAT GTTAT - - - TAGGGT - - - TTGTGACGAG TTCGTCGGCT TTCTAGATAC G-3' (SEQ ID NO:24), BglII site in italics, mutations underlined and deletion shown as lines).

310mut4 was constructed using PSS310-A and PSS310-B4 (5'-CTATAAACAT TCAAAAAAAT GTTAT - - - TAG-GTT - - - TTGGTTTGAT TACGTCGGCT TTCTAGATAC G-3' (SEQ ID NO:25). BglII site in italics, mutations underlined and deletion shown as lines).

310mut5 was obtained using PSS310-A and PSS310-B5 (5'-CTATAAACAT TCAAAAAAAT GTTAT - - - TAGGTT - - - TTGGTTCGAT TACGTCGGCT TTCTA-GATAC G-3' (SEQ ID NO:26), BglII site in italics, mutations underlined and deletion shown as lines).

310mut6 was constructed using primer PSS310-A and PSS310-B6 (5'-GTTATAGTAG TTAGGTTCTA CGA-GTT - - - CGTCTATG ATCTAGATAC G-3' (SEQ ID NO:27), BglII site in italics, mutations underlined and deletion shown as lines).

310mut7 was obtained using primers PSS310-A and PSS310-B2ΔQ (5'-GTTATAGTAG TTAG - - - CTA CGAGTT - - - CGTCGGCT TTCTAGATAC G-3' (SEQ ID NO:28), BglII site in italics, mutations underlined and deletion shown as lines).

310mut8 was produced using primer PSS310-A and PSS310-B2ΔD (5'-GTTATAGTAG TTAGGTT - - - CGAGTT - - - CGTCGGCT TTCTAGATAC G-3' (SEQ ID NO:29), BglII site in italics, mutations underlined and deletion shown as lines).

310mut10 was constructed using primer PSS310-A and PSS310-B21F (5'-CGTTATCGGT GCAAATAAAA AAACTATAAA CATTCAAAAA AATGTTATAG TAGT-TAGGTT CTACGAGTT - - - CGTCG GCTTTCTAGA TACG-3' (SEQ ID NO:30), BglII site in italics, mutations underlined and deletion shown as lines).

310mut11 was obtained using primer PSS310-A and PSS310-B22F (5'-CGTTATCGGT GCAAATAAAA AAACTATAAA CATAAAAAAA AATGTTATAG TAGT-TAGGTT CTACGAGTT - - - CGTCG GCTTTCTAGA TACG-3' (SEQ ID NO:31), BglII site in italics, mutations underlined and deletion shown as lines).

For the construction of 310mutA, primer PSS310-AA (5'-CCTCCCGGGT CTAGATTAGG GTAACTTTGA AAGGATATTC CTCatgAAAT TAATAAAAA AAGAGT-TGCA ATAGCCTTGT TTATTGCTTT GATATTTGTA CTTTTTTTTC TTATATCATC-3' (SEQ ID NO:32), SmaI site in italics, ATG start codon in lower case and mutations underlined) and PSS310-B0 were used.

310mutB was obtained using primer PSS310-AB (5'-CCTCCCGGGT CTAGATTAGG TAACTTTGAAA GGATATTCCTC atgAAATTTTA ATAAAAAAAG AGTT CTTATA CTTTTGTTTA TTCTTTTGAT ATTTGTACTT TTTTTTCTTA TATCATC-3' (SEQ ID NO. 33), SmaI site in italics, ATG start codon in lower case and mutations underlined) and PSS310-B. 310mutC was obtained using primer PSS310-AC (5'-CCTCCCGGGT CTAGATTAGG GTAACTTTGA AAGGATATTC CTCatgAAAT TAATAAAAA AAGACTTTTG CTTTTGCTTT TGCTTTTGCT TTTACTTCTT TTG-3' (SEQ ID NO:34), SmaI site in italics, ATG start codon in lower case and mutations underlined) and PSS310-BC (5'-GAAAATGAAG AAAACGAAAA CGAATATAGT AGTTAGGTTC TAT-TGGTTTG ATTACGTCGG CTTTCTAGAT ACG-3' (SEQ ID NO:35), BglII site in italics and mutations underlined).

310mutA1 was constructed using primer PSS310-AA and PSS310-B1 (5'-GGTTCTATTG GTTCGATTAC GTCG-GCTTTC TAGATACG-3' (SEQ ID NO:36), BglII site in italics and mutation underlined).

310mutA1 was obtained using primer PSS310-AB (5'-CCTCCCGGGT CTAGATTAGG GTAACTTTGA AAG-GATATTC CTCatgAAAT TAATAAAA AAAGAGTTCT TATACTTTTTG TTTATTCTTT TGATATTTGT A CTTTTTTTTT CTTATATCAT C-3' (SEQ ID NO:37), SmaI site in italics, ATG start codon in lower case and mutations underlined) and PSS310-B1.

Construction of 310mutD2 was performed using primer PSS310-AΔF (5'-GCATCCCGGG TCTAGATTAG GGTAACTTTG AAAGGATATT CCTCatgAAA - - - AATAAAA AAAGAGTTGC AATAGCC-3' (SEQ ID NO:38), SmaI site in italics, ATG start codon in lower case, mutations underlined and deletions shown as lines) and PSS310B2.

310mutD7 was constructed using PSS310-AΔF and PSS310-B2ΔQ. 310mut E2 was obtained using primer PSS310-AΔN (5'-GCATCCCGGG TCTAGATTAG GGTAACTTTG AAAGGATATT CCTCatgAAA TTT-AAAA AAAGAGTTGC AATAGCC-3' (SEQ ID NO:39), SmaI site in italics, ATG start codon in lower case and deletions shown as lines) and PSS310-B2.

Construction of 310mutE11 was performed using primer PSS310-AΔF and PSS310-822F.

310mutF2 was constructed using primer PSS310-AK (5'-GCATCCCGGG TCTAGATTAG GGTAACTTTG AAAGGATATT CCTCatgAAA TTT<u>AAA</u>AAAA AAA-GAGTTGC AATAGCC-3' (SEQ ID NO:40), SmaI site in italics, ATG start codon in lower case and mutations underlined) and PSS310-2.

In all cases, clones were introduced in *E. coli* by electroporation, and the presence of mutations in the 310 sequence was confirmed by sequencing both strands using a Thermo Sequenase fluorescently labelled primer cycle sequencing kit (Amersham), Cy5-labelled primers and an ALFexpress DNA Sequencer (Pharmacia Biotech). Plasmid DNA was subsequently introduced into *L. lactis* MG1363.

(iii) Protein Analysis and SDS-PAGE

Culture supernatants were concentrated 20- to 30-fold using the Phenol-Ether procedure (Sauvé et al., 1995). Samples were run on 16% Tricine gels (Novex), according to the manufacturer. The gels were stained overnight using the Colloidal Coomassie Staining Kit (Novex). The Mark 12 Wide Range Standard (Novex) was used to estimate molecular sizes.

(iv) Protein Sequence Analysis

Derivatives of SP310 were analysed using the SignalP WWW server (Nielsen et al. 1997) to predict their suitability as SP.

(v) Fermentation

Fermentation experiments were carried out using bench top fermentors (Applikon), containing 1 liter of medium and set to operate at 30° C. and to maintain the pH above 5.2.

2.3. Results (i) An Experimental Setup for the Analysis of Secretion Efficiency in *L. lactis*

In Example 1 a number of novel SPs were constructed using insertional mutagenesis with a Tn917 derivative containing the nuc gene. Among these, SP310 was selected for further work since its use resulted in the highest yields of Nuclease (Nuc) secretion, when expression of the SP310-nuc gene fusion was driven by promoter P170 on a multi-copy plasmid. Compared to the SP from Usp45 (SPUSP), the major secreted lactococcal protein, the Nuc secretion yield obtained using SP310 was significantly lower.

In order to improve the secretion level of SP310 and to allow for the easy identification of mutants with enhanced secretion of Nuc, the levels of Nuc in culture supernatants from overnight cultures grown in GM17 were compared to the level obtained during growth in fermentor in SAIV medium. As shown, the use of the minimal SP 35 aa wild type sequence including the Ala at position +1 (Ala$^{+1}$, the N-terminal aa of the processed protein) resulted in a secretion level of 5,67 mg/L of Nuc. This represents about 78% of the level observed using SPUSP (strain PRA76) after overnight growth in GM17 (Table 3). Total values of secreted Nuc were lower than the Nuc levels obtained in fermentor, but the relative efficiency of SP310 was in the same order of magnitude compared to SPUSP, i.e. over 58% (106 vs. 182 mg/L respectively). Thus, it was decided to measure Nuc secretion in overnight culture supernatants grown in GM17 for the initial screening of SP310 mutants.

Overall, about 20-fold decrease in the total amount of Nuc secretion was obtained in GM17 overnight cultures compared to fermentors. This is mainly due to different regulation of the P170 promoter, the unequal physiological conditions and the media used. For SP310, 5,67 mg/L were measured in GM17 culture supernatants and 106 mg/L in fermentor. The results of the GM17 cultures are summarised in table 3.

| SEQ ID NO: | Name | Sequence | Nuc (mg/L) | % |
|---|---|---|---|---|
| 41 | SP310 | M K F N K K R V A I A T F I A L I F V S F F T I S S I Q D N Q T N A A E R S | 5.67 ± 1.20 | 100 |
| 42 | 310mut1 | M K F N K K R V A I A T F I A L I F V S F F T I S S I Q D N Q <u>A</u> N A A E R S | 6.40 ± 0.66 | 113 |
| 43 | 310mut2 | M K F N K K R V A I A T F I A L I F V S F F T I S S I Q D <u>A</u> Q <u>=</u> <u>=</u> A A E R S | 7.03 ± 0.74 | 124 |
| 44 | 310mut3 | M K F N K K R V A I A T F I A L I F V S F F T I - - I <u>P</u> <u>=</u> N <u>T</u> <u>AQ</u> A A E R S | 6.16 ± 0.03 | 109 |
| 45 | 310mut4 | M K F N K K R V A I A T F I A L I F V S F F T I - - I <u>P</u> <u>=</u> N <u>T</u> <u>AQ</u> A A E R S | 3.93 ± 0.72 | 69 |
| 46 | 310mut5 | M K F N K K R V A I A T F I A L I F V S F F T I - - I Q <u>=</u> N Q <u>A</u> N A A E R S | 3.90 ± 0.97 | 69 |
| 47 | 310mut6 | M K F N K K R V A I A T F I A L I F V S F F T I S S I Q D <u>A</u> Q <u>=</u> <u>=</u> <u>A</u> D <u>T</u> R S | 6.40 ± 0.49 | 113 |
| 48 | 310mut7 | M K F N K K R V A I A T F I A L I F V S F F T I S S I - D <u>A</u> Q <u>=</u> <u>=</u> A A E R S | 5.01 ± 0.08 | 88 |
| 49 | 310mut8 | M K F N K K R V A I A T F I A L I F V S F F T I S S I Q D <u>=</u> <u>A</u> Q <u>=</u> <u>=</u> A A E R S | 3.44 ± 1.27 | 61 |
| 51 | 310mut10 | M K F N K K R V A I A T F I <u>F</u> L I F V S F F T I S S I Q D <u>A</u> Q - <u>=</u> A A E R S | 5.52 ± 1.33 | 97 |
| 53 | 310mutA | M K F N K K R V A I A <u>L</u> F I A L I F V <u>L</u> F F <u>L</u> I S S I Q D N Q T N A A E R S | 2.64 ± 0.74 | 46 |
| 54 | 310mutB | M K F N K K R V <u>L</u> I <u>L</u> <u>L</u> F I <u>L</u> L I F V <u>L</u> F F <u>L</u> I S S I Q D N Q T N A A E R S | 2.30 ± 0.50 | 41 |
| 55 | 310mutC | M K F N K K R <u>L</u> <u>L</u> <u>L</u> <u>L</u> <u>L</u> <u>L</u> <u>L</u> <u>L</u> <u>L</u> <u>L</u> <u>L</u> <u>L</u> <u>L</u> <u>L</u> <u>L</u> I S S I Q D N Q T N A A E R S | 1.99 ± 0.03 | 35 |
| 56 | 310mutA1 | M K F N K K R V A I A <u>L</u> F I A L I F V <u>L</u> F F <u>L</u> I S S I Q <u>A</u> N Q T N A A E R S | 3.60 ± 0.58 | 63 |
| 57 | 310mutB1 | M K F N K K R V <u>L</u> I <u>L</u> <u>L</u> F I <u>L</u> L I F V <u>L</u> F F <u>L</u> I S S I Q <u>A</u> N Q T N A A E R S | 2.21 ± 0.02 | 39 |

-continued

| SEQ ID NO: | Name | Sequence | Nuc (mg/L) | % |
|---|---|---|---|---|
| 58 | 310mutD2 | M K _ N K K R V A I A T F I A L I F V S F F T I S S I Q D A Q _ _ A A E R S | 6.31 ± 1.41 | 111 |
| 59 | 310mutD7 | M K _ N K K R V A I A T F I A L I F V S F F T I S S I _ D A Q _ _ A A E R S | 5.79 ± 1.03 | 102 |
| 60 | 310mutE2 | M K F _ K K R V A I A T F I A L I F V S F F T I S S I Q D A Q _ _ A A E R S | 7.02 ± 0.17 | 124 |
| 61 | 310mutE11 | M K _ N K K R V A I A T F I F L I F V F F F T I S S I Q D A Q _ _ A A E R S | 3.62 ± 1.15 | 64 |
| 62 | 310mutF2 | M K F K K K R V A I A T F I A L I F V S F F T I S S I Q D A Q _ _ A A E R S | 1.40 ± 0.25 | 25 |
|  | SPUSP |  | 7.27 ± 0.07 | 128 |

Nuclease yields from two independent growth experiments are shown as mg/L and as percentage of the activity shown by the wild type SP310 (100%).
An open box in the SP310 sequence depicts the suggested hydrophobic core of the signal sequence.
The values obtained for SPUSP (strain AMJ627) are also shown at the bottom.
The sequences 310mut0—310mutF2 are included as SEQ ID NO:41—49, 51, and 53—62.

(ii) Site-Directed Mutagenesis of the *L. lactis* SP310 Signal Sequence

Initial analysis of the primary SP310 aa sequence was carried out using SignalP. Efficient bacterial SPs show an Ala at position −3, −1 and +1. The sequence of SP310 included a Thr, a relatively infrequent aa, at position −3 (Thr$^{-3}$). As shown, substitution of the Thr$^{-3}$ residue to Ala$^{-3}$ (in strain 310mut1) resulted in a significant increase in Nuc secretion (Table 3). It was evident that the C-terminal region of SP310 (FIG. 3), was unusually long and included a number of residues (position −10 to −2; Ser$^{-9}$, Ser$^{-10}$, Asn$^{-5}$, Gln$^{-4}$, Gln$^{-7}$, Asp$^{-6}$ and Thr$^{-3}$) normally not present in this domain of Gram-positive SPs. Deletion of Thr$^{-3}$ and Asn$^{-2}$ and substitution of Asn$^{-5}$ to Ala$^{-3}$ was therefore incorporated into 310mut2. This mutant retains Ala at position −3, −1 and +1 (FIG. 3). Analysis of Nuc secretion in 310mut2 showed an increase of up to 24% compared to the wild type SP310 and also an increase with respect to the levels observed with 310mut1 in overnight cultures grown in GM17 (Table 3). These results confirmed that shortening of the C-terminal region and maintenance of Ala residues at the cleavage site resulted in a considerable improvement in Nuc secretion in *L. lactis*.

The analysis of SP from Gram-positive bacteria using SignalP predicted that a turn favoring aa (e.g. Gly or Pro) is often located at the position between the hydrophobic core and the C-terminal domain. In SP310, two Ser residues (Ser$^{-10}$ and Ser$^{-9}$) are located in this region. We constructed a mutant lacking these two residues and Asp$^{-6}$ (310mut4). These alterations resulted in a considerable reduction in the level of Nuc compared to SP310 (Table 3), suggesting that the presence of Ser and/or Asp in the C-terminal region of SP310 is a requirement for effective secretion in *L. lactis*. A single substitution in 310mut4 to incorporate an Ala residue at position −3 (in 310mut5) did not affect secretion efficiency (Table 3), strongly pointing out the essential role of these residues. However, substitution of Asn$^{-2}$, Gln$^{-4}$ to more frequent aa found at these positions (Gln$^{-2}$ and Thr−4), together with a substitution of Gln$^{-6}$ to Pro$^{-6}$ in 310mut3 resulted in a higher level of secretion as compared to SP310, but lower than 310mut2. Pro is also found in this region in the SP of two major extracellular *L. lactis* proteins, PrtP and Usp45 (Table 4 below) and the results obtained with 310mut3 support the role of this aa in secretion. Interestingly, a double Ser is also present in this region in Exp2, another *L. lactis* extracellular protein whose SP was recently identified (Poquet et al., 1998).

| SEQ ID NO | Protein | Charge Charge | Hydrophobic Core | Processing Region | Mature Protein |
|---|---|---|---|---|---|
| 41 | SP310 | MKFNKKR | VAIATFIALIFVSFFTI | SSIQDNQT-NAAERS | AERS |
| 43 | *310mut2* | *MKFNKKR* | *VAIATFIALIFVSFFTI* | *SSIQDAQA* | *AERS* |
| 63 | Usp45 | MKKKIIS | AILMSTVJLSAAA | PLSGVYA | DTNSD |
| 64 | PrtP | MQRKKKG | LSILLAGTVALGALAVL | PVGEIQAKA | AISQQ |
| 65 | Exp1 | MKNLIPKKIKQ | VGILVGALLMLLSVLPVNLL | GVMKVDA | DSSQTEV |
| 66 | Exp2 | MKK | IAIIFCTLLMSLSVL | SSFAVSA | DTTTTTNN |

Analysis of additional changes designed to shorten the C-terminal region by removing either Gln$^{-7}$ (strain 310mut7) or Asp$^{-6}$ (strain 310mut8) resulted in a significant decrease in secretion (Table 3). It remains unclear whether the length change or the alteration in charge in the C-terminal region is responsible for the decrease in secretion efficiency.

The N-terminal residues of the mature protein may also be important for effective processing by the secretion machinery. In the L. lactis Usp45 and Exp2, Asp and Thr are the first two aa in the processed protein (Table 4). Thus, a mutant was studied that included these two aa at position +1 and +2, preserving the sequence of 310mut2 in the SP. As shown, this mutant, 310mut6 secreted a slightly lower amount of Nuc compared to 310mut2, although the levels obtained were higher compared to SP310 (Table 3).

A series of mutants were constructed and characterized to study the role of the hydrophobic core in secretion in L. lactis. In E. coli, the hydrophobic core appears to effect an essential role in secretion, and increasing the hydrophobicity of this region compensates defects in either the N-terminus or the processing region (REF). Therefore, substitution of $Ala^{-20}$ alone (in 310mut10) or in combination with $Ser^{-15}$ (strain 310mut11) to Phe was analyzed. As shown, a correlation between the decrease in secretion efficiency and the number of Phe introduced was observed. Nuc secretion in strain 310 mut11 was much lower than in 310mut2 and slightly lower than SP310 (Table 3).

In E. coli the presence of Leu in the hydrophobic region has also proven as an enhancer of secretion. A series of mutants were therefore constructed that included three, six or fourteen Leu residues in addition to the $Leu^{-19}$ present in SP310. In 310mutA, 310mutB and 310mutC, Leu was introduced at different positions in the hydrophobic region maintaining the wild type sequence at the C-terminal region (Table 3). A large reduction in efficiency (46% compared to SP310) was observed in 310mutA, and even lower yields were obtained in 310mutB (41%) and 310mutC (35%), indicating that increasing amounts of Leu result in a gradual decrease in the secretion level. A modified version of 310mutA and 310mutB that incorporated also an Ala at position −3 (corresponding to the C-terminal region of 310mut1) was studied. (n one of these mutants, 310mutA1, the level of secretion was somewhat higher (63% compared to SP310) indicating that conserved Ala positions in the processing region partially compensate the presence of moderate excess Leu in the hydrophobic core in L. lactis. However when six Leu were present (strain 310mut1), the yield obtained was similar to 310mutB, indicating that the higher Leu content in the hydrophobic core cannot be compensated by the presence of $Ala^{-3}$ (Table 3).

A series of mutants was constructed to investigate the influence of the N-terminal region in secretion. In this series, the C-terminal region of 310mut2 (or 310mut7) was used and removal of Phe or Asn from the N-terminal region was carried out, to increase the overall positive charge. In 310mutD2, removal of $Phe^{-33}$ resulted in secretion levels higher than SP310 but lower than 310mut2 (Table 3). When the C-terminal region of 310mut7 was used an even lower yield was obtained, providing additional evidence that the lack of $Gln^{-7}$ is attenuated in a SP carrying a shorter or more polar N-terminal region. Removal of $Asn^{-32}$ (strain 310mutE2) resulted in maximal levels of secretion identical to 310mut2 (Table 3), suggesting a minimal role of this residue in efficiency. A dramatic decrease was observed when the hydrophobic and C-terminal region of 310 mut11 were combined with the N-terminal region of 310 mutD2 in strain 310mutE11, strongly confirming the main role of the hydrophobic core in the overall performance during secretion (Table 3). In strain 310 mutF2, the N-terminal region was modified by substitution of $Asn^{-32}$ to Lys, to increase the net positive charge. This alteration resulted in the lowest level of Nuc secretion observed among all mutants analysed (Table 3). Thus, the net charge of the N-terminal region of SP310 might represent the maximum allowed for efficient secretion in L. lactis.

(ii) Processing and Secretion of Nuc Using SP310 and Selected Mutants

Supernatants from overnight cultures of AMJ627, PRA159 and mutants PRA164, 310mutB and 310mutB were analysed in SDS-PAGE. In AMJ627, a strong band corresponding in size to the processed Nuc protein was observed, in addition to the main 45 kDa Usp45 protein (FIG. 4, lane 1). For PRA159, the gene fusion includes the full length SP310 and 25 additional codons corresponding to the N-terminus of the processed protein (Example 1). A main 19 kD band was observed that is the expected size of a full length Nuc with a 25 aa N-terminal extension. Minor bands in this preparation might correspond to further processing of the fusion protein into full-length Nuc (a 16 kDa band was detected; FIG. 4, lane 2). In strain PRA164, the presence of two major Nuc bands supported the alternative processing site suggested by the sequence analysis using SignalP (FIG. 3). A single Nuc band was detected in PRA164. 310mutB and 310mut6, indicating that a single processing site is used in these mutants. The relative amounts of Nuc were in agreement with the activity levels measured in these strains (Table 3).

(iii) Analysis of Nuc Secretion in Fermentor

As mentioned above, the production levels using the P170-dependent expression system of L. lactis are at least 20-fold higher during controlled growth in defined medium in fermentor as compared to the levels obtained in overnight cultures grown in rich GM17 medium. Therefore, the wild type SP310 and three mutants representing maximal (310mut2), middle (310mut6) or low (310mutB) secretion efficiency were used in comparison to AMJ627 (SPUSP). As shown, 310mut2 yielded over 150 mg/L Nuc representing a 45% improvement with respect to SP310 (Table 5 below). For 310mut6, the values obtained confirmed a better performance (25% improvement compared to SP310) and 310mutB yielded 50% of the amount secreted using SP310 resembling the results of the initial screening in GM17. Interestingly, the yield of 310mut2 in fermentor is comparable to SPUSP, reaching 85% of the amount of Nuc secreted by the latter.

TABLE 5

Nuclease secretion in fermentor

| Strain (SP) | Nuc (mg/L) | Relative amount (%) |
|---|---|---|
| PRA162 (310mut0) | 106 ± 1.7 | 100 |
| PRA164 (310mut2) | 154 ± 3.1 | 145 |
| PRA250 (310mut6) | 132 ± 0.2 | 125 |
| PRA170 (310mutB) | 54 ± 3.3 | 51 |
| AMJ627 (SPUSP) | 182 ± x.x | 172 |

Strains were grown in SAIV in a fermentor set at 30° C., pH 5.2.

REFERENCES

Ashbaugh, C. D., Alberti, S. and Wessels, M. R. (1998) Molecular analysis of the capsule gene region of group A Streptococcus: the hasAB genes are sufficient for capsule expression. J Bacteriol 180:4955–4959.

Camilli, A., Portnoy, A. and Youngman, P. (1990) Insertional mutagenesis of Listeria monocytogenes with a novel Tn917 derivative that allows direct cloning of DNA flanking transposon insertions. *J Bacteriol* 172:3738–3744.

Chen, M., and Nagarajan, V. (1994) Effect of alteration of charged residues at the N termini of signal peptides on protein export in *Bacillus subtilis. J Bacteriol* 176:5796–5801.

Chen, H., Kim, J., and Kendall, D. A. (1996) Competition between functional signal peptides demonstrates variation in affinity for the secretion pathway. *J Bacteriol* 178: 6658–6664.

Collier, D. N. (1994) *Escherichia coli* signal peptides direct inefficient secretion of an outer membrane protein (OmpA) and periplasmic proteins (maltose-binding protein, ribose-binding protein, and alkaline phosphatase) in *Bacillus subtilis. J Bacteriol* 176:3013–3020.

Gasson, M. (1983) Plasmid complements of *Streptococcus lactis* NCDO712 and other lactic streptococci after protoplast-induced curing. *J Bacteriol* 154:1–9.

Godon, J. J., Jury, K., Shearman, C. A. and Gasson M. J. (1994) The *Lactococcus lactis* sex-factor aggregation gene cluA. *Mol Microbiol* 12:655–663

Grant, S. G., Jesse, J., Bloom, F. R. and Hanahan, D. (1990) Differential plasmid rescue from transgenic mouse DNAs into *Escherichia coli* methylation-restriction mutants. *Proc Natl Acad Sci* USA 87:4645–4649.

Holo, H., and Nes, I. F. (1989) High-frequency transformation, by electroporation of *Lactococcus lactis* subsp. *cremoris* grown with glycine in osmotically stabilized media. *Appl Environ Microbiol* 55:3119–3123.

Israelsen, H. and Hansen, E. B. (1993) Insertion of transposon Tn917 derivatives into the *Lactococcus lactis* subsp. *lactis* chromosome. *Appl Environ Microbiol* 59:21–26.

Israelsen, H., Madsen, S. M., Vrang, A., Hansen, E. B., and Johansen, E. (1995) Cloning and partial characterization of regulated promoters from *Lactococcus lactis* Tn917-lacZ integrants with the new promoter probe vector pAK80. *Appl Environ Microbiol* 61:2540–2547.

Jensen, P. R., and Hammer, K. (1993) Minimal requirements for exponential growth *Lactococcus lactis. Appl Environ Microbiol* 59:4363–4366.

Izard, J. W., Doughty, M. B., Kendall, D. A. (1995) Physical and conformational properties of synthetic idealized signal sequences parallel their biological function. *Biochemistry* 34:9904–9912.

Izard, J. W., Rusch, S. L., and Kendall, D. A. (1996) The amino-terminal charge and core region hydrophobicity interdependently contribute to the function of signal sequences. *J Biol Chem* 271:21579–21582.

Lachica, R. V., Genigeorgis, C. and Hoeprich, P. D. (1971) Metachromatic agardiffusion methods for detecting staphylococcal nuclease activity. *Appl Microbiol* 21:585–587.

Le Loir, Y., Gruss, A., Ehrlich, S. D., and Langella, P. (1994) Direct screening of recombinants in gram-positive bacteria using the secreted staphylococcal nuclease as a reporter. *J Bacteriol* 176:5135–5139.

Madsen S. M., Albrechtsen, B., Hansen, E. B. and Israelsen, H. (1996) Cloning and transcriptional analysis of two threonine biosynthetic genes from *Lactococcus lactis* MG1614. *J Bacteriol* 178:3689–3694

Madsen, S. M., Arnau, J., Vrang, A., Givskov, M., and Israelsen, H. (1999) Molecular characterization of the pH-inducible and growth phase-dependent promoter P170 of *Lactococcus lactis. Mol Microbiol* 32:75–87.

Martoglio, B., and Dobberstein, B. (1998) Signal sequences: more than just greasy peptides. *Trends Cell Biol* 8:410–415.

Nielsen, H., Engelbrecht, J., Brunak, S., and von Heijne, G. (1997) A neural network method for identification of prokaryotic and eukaryotic signal peptides and prediction of their cleavage sites. *Int. Neural Sys* 8:581–599.

Poquet, I., Ehrlich, S. D., and Gruss, A. (1998) An export-specific reporter designed for gram-positive bacteria: application to *Lactococcus lactis. J Bacteriol* 180:1904–1912.

Ravn, P., Arnau, J., Madsen, S., Vrang, A., and Israelsen, H. (1999) The development of TnNuc and its use for the isolation of novel secretion signals in *Lactococcus lactis.* (in press)

Sambrook, J., Fritsch, E. F., and Maniatis, T. (1989) Molecular cloning: a laboratory manual, 2nd ed. Cold Spring Harbor Laboratory, Cold Spring Harbor, N.Y.

Santini, C. L., Ize, B., Chanal, A., Muller, M., Giordano, G. Wu, L. F. (1998) A novel sec-independent periplasmic protein translocation pathway in *Escherichia coli. EMBO J* 17:101–112.

Sauve D. M., Ho, D. T. and Roberge, M. (1995) Concentration of dilute protein for gel electrophoresis. *Anal Biochem* 226:382–383.

Settles, A. M., and Martienssen, R. (1998) Old and new pathways of protein export in chloroplasts and bacteria. *Trends Cell Biol* 8:494–501

Sherrat, D. (1989) Tn3 and related transposable elements: site-specific recombination and transposition. In: Berg, E. D. and Howe, M. M. (eds.) Mobile DNA, American Society for Microbiology, Washington D.C., USA, pp. 163–184.

Stephens, C. (1998) Protein secretion: getting folded proteins across membranes. *Curr Biol* 8:578–581.

Takimura, Y., Kato, M., Ohta, T., Yamagata, H., and Udaka, S. (1997) Secretion of human interleukin-2 in biologically active form by *Bacillus brevis* directly into culture medium. *Biosci Biotechnol Biochem* 61:1858–1861.

van Asseldonk M., Rutten, G., Oteman, M., Siezen, R. J., de Vos, W. M. and Simons G. (1990) Cloning of usp45, a gene encoding a secreted protein from *Lactococcus lactis* subsp. *lactis* MG1363. *Gene* 95:155–60.

van Asseldonk M., de Vos. W. M., and Simons, G. (1993) Functional analysis of the *Lactococcus lactis* usp45 secretion signal in the secretion of a homologous proteinase and a heterologous alpha-amylase. *Mol Gen Genet* 240: 428–434.

von Heijne, G. (1990) The signal peptide. *J Mol Biol* 115:195–201.

Wang, L. F., Kortt, A. A. and Stewart, D. J. (1993) Use of a gram-signal peptide for protein secretion by gram+hosts: basic protease of *Dichelobacter nodosus* is produced and secreted by *Bacillus subtilis. Gene* 131:97–102.

Weiner, J. H., Bilous, P. T., Shaw, G. M., Lubitz, S. P., Frost, L., Thomas, G. H., Cole, J. A. and Turner, R. J. (1998) A novel and ubiquitous system for membrane targeting and secretion of cofactor-containing proteins. *Cell* 93:93–101.

Whiting. G. C., Sutcliffe, I. C. and Russell, R. R. (1993) Metabolism of polysaccharides by the *Streptococcus mutants* dexB gene product. *J Gen Microbiol* 139:2019–2026.

Youngman, P. (1987) Plasmid vectors for recovering and exploiting Tn917 transpositions in *Bacillus* and other Gram-positive bacteria. In: Hardy, K. G. (ed) Plasmids, a practical approach, IRL Press, Oxford, UK, pp. 79–103.

The invention claimed is:

1. An isolated DNA molecule comprising: (i) at least part of a transposon derivative including between its left terminus (LR) and its right terminus (RR) a sequence comprising a promoterless promoter reporter gene, a ribosome binding site and a secretion reporter gene without a sequence coding for a signal peptide (SP), the DNA molecule being without stop codons in the region upstream from the secretion reporter gene and (ii) a DNA sequence coding for a signal peptide selected from the group consisting of SP310 (SEQ ID NO:41), 310mut1 (SEQ ID NO:42), 310mut2 (SEQ ID NO:43), 310mut3 (SEQ ID NO:44), 310mut4 SEQ ID NO:45), 310mut5 (SEQ ID NO:46), 310mut6 (SEQ ID NO:47), 310mut7 (SEQ ID NO:48), 310mut8 (SEQ ID NO:49), 310mut10 (SEQ ID NO:51), 310mut11 (SEQ ID NO:52), 310mutA (SEQ ID NO:53), 310mutB (SEQ ID NO:54), 310mutC (SEQ ID NO:55), 310mutA1 (SEQ ID NO:56), 310mutB1 (SEQ ID NO:57), 310mutD2 (SEQ ID NO:58), 310mutD7(SEQ ID NO:59), 310mutE2 (SEQ ID NO:60), 310mutE11(SEQ ID NO:61) and 310mutF2 (SEQ ID NO:62).

2. The DNA molecule of claim 1, wherein the signal peptide comprises a signal peptidase I-recognition sequence.

3. The DNA molecule of claim 1, wherein the signal peptide comprises a signal peptidase II-recognition sequence.

4. An isolated DNA sequence coding for a signal peptide selected from the group consisting of SP310 (SEQ ID NO:41), 310mut1 (SEQ ID NO:42), 310mut2 (SEQ ID NO:43), 310mut3 (SEQ ID NO:44), 310mut4 (SEQ ID NO:45), 310mut5 (SEQ ID NO:46), 310mut6 (SEQ ID NO:47), 310mut7 (SEQ ID NO:48), 310mut8 (SEQ ID NO:49), 310mut10 (SEQ ID NO:51), 310mut11 (SEQ ID NO:52), 310mutA (SEQ ID NO:53), 310mutB (SEQ ID NO:54), 310mutC (SEQ ID NO:55), 310mutA1 (SEQ ID NO:56), 310mutB1 (SEQ ID NO:57), 310mutD2 (SEQ ID NO:58), 310mutD7(SEQ ID NO:59), 310mutE2 (SEQ ID NO:60), 310mutE11(SEQ ID NO:61) and 310mutF2 (SEQ ID NO:62).

5. A recombinant plasmid comprising the isolated DNA molecule according to claim 1.

6. The recombinant plasmid of claim 5 that further comprises a regulatable promoter operably linked to a nuc gene.

7. A plasmid according to claim 6 wherein the regulatable promoter is P170.

8. A recombinant bacterium comprising a DNA sequence according to claim 4.

9. The bacterium of claim 8 wherein the DNA sequence is operably linked to a gene expressing a desired gene product whereby the gene product is secreted.

10. The bacterium of claim 8, wherein the bacterium is a lactic acid bacterium.

11. A method of producing a desired gene product comprising inserting a gene coding for the desired gene product into a host organism comprising the bacterium of claim 8 and expressing the gene product.

12. The method of claim 11, wherein the bacterium is a lactic acid bacterium.

13. A recombinant plasmid comprising an isolated DNA molecule comprising an isolated DNA sequence according to claim 4.

* * * * *